United States Patent
Deo et al.

(10) Patent No.: US 11,950,961 B2
(45) Date of Patent: Apr. 9, 2024

(54) AUTOMATED CARDIAC FUNCTION ASSESSMENT BY ECHOCARDIOGRAPHY

(71) Applicant: The Regents of the University of California, Oakland, CA (US)

(72) Inventors: Rahul C. Deo, Needham, MA (US); Jeffrey Zhang, Dublin, CA (US)

(73) Assignee: The Regents of the University of California, Oakland, CA (US)

(*) Notice: Subject to any disclaimer, the term of this patent is extended or adjusted under 35 U.S.C. 154(b) by 860 days.

(21) Appl. No.: 16/977,418

(22) PCT Filed: Mar. 14, 2019

(86) PCT No.: PCT/US2019/022342
§ 371 (c)(1),
(2) Date: Sep. 1, 2020

(87) PCT Pub. No.: WO2019/178404
PCT Pub. Date: Sep. 19, 2019

(65) Prior Publication Data
US 2021/0000449 A1    Jan. 7, 2021

Related U.S. Application Data

(60) Provisional application No. 62/642,930, filed on Mar. 14, 2018.

(51) Int. Cl.
A61B 8/00    (2006.01)
A61B 8/06    (2006.01)
(Continued)

(52) U.S. Cl.
CPC ............ *A61B 8/5223* (2013.01); *A61B 8/065* (2013.01); *A61B 8/461* (2013.01); *A61B 8/485* (2013.01);
(Continued)

(58) Field of Classification Search
CPC ....... A61B 8/5223; A61B 8/065; A61B 8/461; A61B 8/485; G06T 2207/20076;
(Continued)

(56) References Cited

U.S. PATENT DOCUMENTS 6,708,055 B2    3/2004  Geiser et al.
7,689,283 B1    3/2010  Schecter
(Continued)

FOREIGN PATENT DOCUMENTS

WO    2017/091833    6/2017
WO    2019/178404    9/2019

OTHER PUBLICATIONS

Application No. PCT/US2019/022342, International Search Report and Written Opinion, dated Jun. 14, 2019, 7 pages.
(Continued)

*Primary Examiner* — Joel F Brutus
(74) *Attorney, Agent, or Firm* — Kilpatrick Townsend & Stockton LLP

(57) ABSTRACT

A computer vision pipeline is provided for fully automated interpretation of cardiac function, using a combination of machine learning strategies to enable building a scalable analysis pipeline for echocardiogram interpretation. Videos from patients with heart failure can be analyzed and processed as follows: 1) preprocessing of echo studies; 2) convolutional neural networks (CNN) processing for view identification; 3) segmentation of chambers and delineation of cardiac boundaries using CNNs; 4); particle tracking to compute longitudinal strain; and 5) targeted disease detection.

18 Claims, 12 Drawing Sheets

(51) Int. Cl.
- *A61B 8/08* (2006.01)
- *G06N 3/08* (2023.01)
- *G06T 7/00* (2017.01)
- *G16H 30/40* (2018.01)
- *G16H 50/20* (2018.01)

(52) U.S. Cl.
CPC ............ *G06N 3/08* (2013.01); *G06T 7/0014* (2013.01); *G16H 30/40* (2018.01); *G16H 50/20* (2018.01); *G06T 2207/20076* (2013.01); *G06T 2207/20081* (2013.01); *G06T 2207/20084* (2013.01); *G06T 2207/30048* (2013.01)

(58) Field of Classification Search
CPC . G06T 2207/20081; G06T 2207/20084; G06T 2207/30048
See application file for complete search history.

(56) References Cited

U.S. PATENT DOCUMENTS

| | | | |
|---|---|---|---|
| 7,693,315 B2 | 4/2010 | Krishnan et al. | |
| 7,912,528 B2 | 3/2011 | Krishnan et al. | |
| 9,968,257 B1 * | 5/2018 | Burt .................... | A61B 5/0035 |
| 2017/0360412 A1 | 12/2017 | Rothberg et al. | |

OTHER PUBLICATIONS

GN Balaji et al., "Automatic classification of Cardiac Views in Echocardiogram using Histogram and Statistical Features," Procedia Computer Science 46 ( 2015 ) 1569-1576.

H. Khamis et al., "Automatic apical view classification of echocardiograms using a discriminative learning dictionary," Med Image Anal. Feb. 2017;36:15-21.

A. Madani et al., "Fast and accurate classification of echocardiograms using deep learning" arXiv: 1706.08658 [cs.CV], Jun. 2017.

JH Park et al., "Automatic Cardiac View Classification of Echocardiogram," J. H. Park, S. K. Zhou, C. Simopoulos, J. Otsuki and D. Comaniciu, "Automatic Cardiac View Classification of Echocardiogram," 2007 IEEE 11th International Conference on Computer Vision, Rio de Janeiro, Brazil, 2007, pp. 1-8, doi: 10.1109/ICCV.2007.4408867.

E. Smistad et al., "2D left ventricle segmentation using deep learning," 2017 IEEE International Ultrasonics Symposium (IUS), Washington, DC, USA, 2017, pp. 1-4, doi: 10.1109/ULTSYM.2017.8092573.

Zhang et al., "A Computer Vision Pipeline for Automated Determination of Cardiac Structure and Function and Detection of Disease by Two-Dimensional Echocardiography," arXiv:1706.07342v7 [cs.CV 12] Jan. 2018, 14 pages.

* cited by examiner

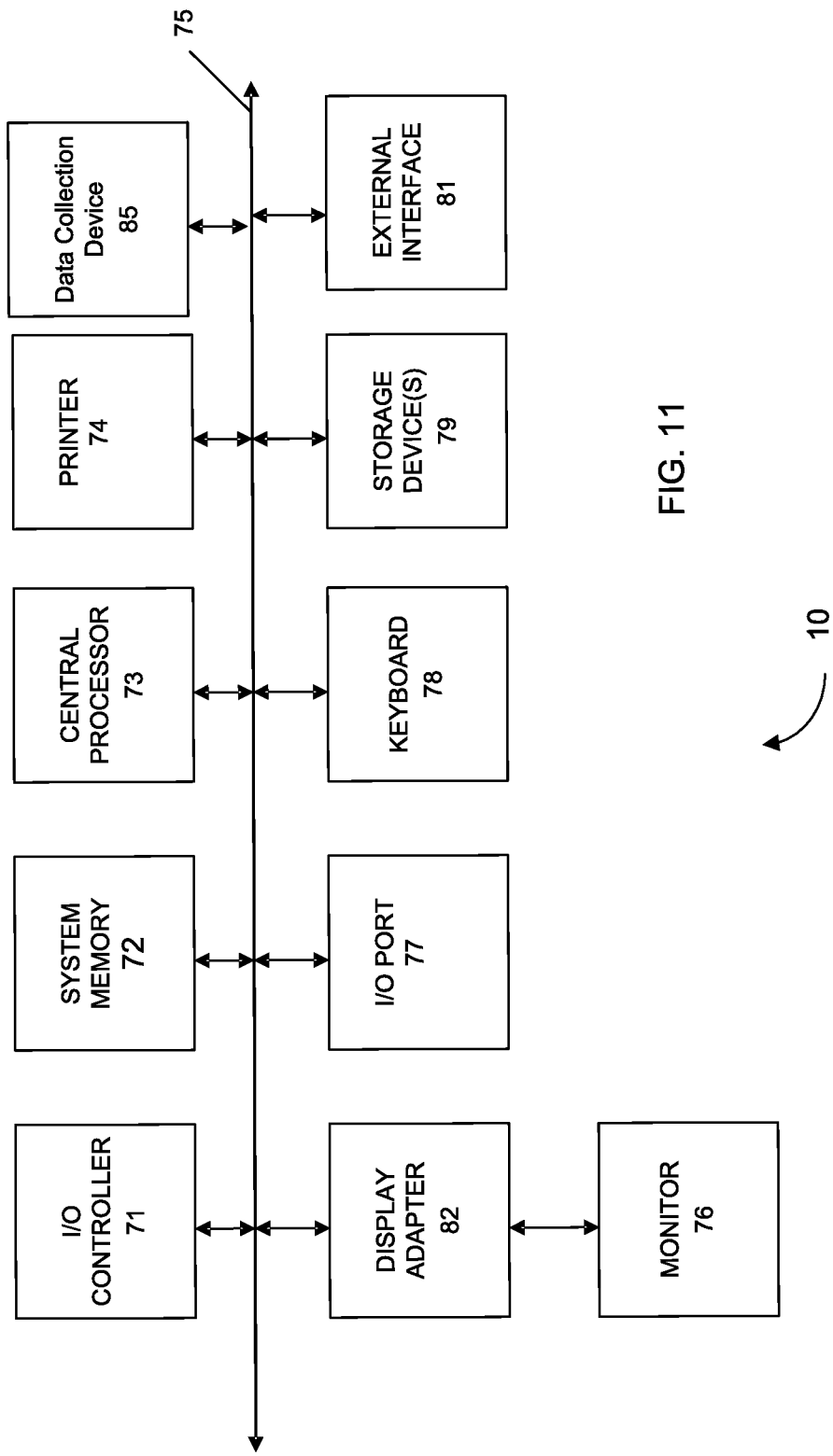

AUTOMATED CARDIAC FUNCTION ASSESSMENT BY ECHOCARDIOGRAPHY

CROSS-REFERENCES TO RELATED APPLICATIONS

The present application claims priority from and is a PCT application of U.S. Provisional Application No. 62/642,930, entitled "Automated Cardiac Function Assessment By Echocardiography" filed Mar. 14, 2018, the entire contents of which are herein incorporated by reference for all purposes.

STATEMENT AS TO RIGHTS TO INVENTIONS MADE UNDER FEDERALLY SPONSORED RESEARCH AND DEVELOPMENT

This invention was made with government support under grant no. HL123228 awarded by the National Institutes of Health. The government has certain rights in the invention.

BACKGROUND

Cardiac remodeling preceding cardiovascular disease often starts long before irreversible pathologic changes occur. Echocardiography is widely available, non-radiation emitting and easy to perform at the bedside, making this method the most widely used noninvasive imaging technique in cardiology. Such evidence of early remodeling can relatively easily be detected by echocardiographic imaging and is potentially trackable longitudinally in individual patients. The ability to gain functional and structural insights about the myocardium can help guide cardiac interventions in real time in a patient-specific manner. However, the cost of imaging each individual with cardiac risk factors over time is currently prohibitive to incorporating this approach into the standard cardiovascular health practice.

Accordingly, it is desirable for improved techniques for echocardiography image analysis to help lower the costs for such longitudinal monitoring.

BRIEF SUMMARY

Some embodiments provide a computer vision pipeline for fully automated interpretation of cardiac function, using a combination of machine learning strategies to enable building a scalable analysis pipeline for echocardiogram interpretation. Apical videos from patients with heart failure can be analyzed and processed as follows: 1) auto-downloading of echo studies, metadata extraction, de-identification, and conversion of images into numerical arrays; 2) convolutional neural networks (CNN) processing for view identification; 3) segmentation of chambers and delineation of cardiac boundaries using CNNs; 4); particle tracking to compute longitudinal strain; and 5) targeted disease detection.

Embodiments can allow high accuracy (>98%) of image identification using the CNN. This lays the groundwork for using automated interpretation to support the use of handheld cardiac ultrasound in primary care practices and may enable large-scale analysis of collected echocardiograms already archived within the healthcare system. Example embodiments comprise a fully automated cardiac echocardiogram interpretation system that can be deployed on the web.

These and other embodiments of the invention are described in detail below. For example, other embodiments are directed to systems, devices, and computer readable media associated with methods described herein.

A better understanding of the nature and advantages of embodiments of the present invention may be gained with reference to the following detailed description and the accompanying drawings.

BRIEF DESCRIPTION OF THE DRAWINGS

FIG. 11 shows a block diagram of an example computer system usable with systems and methods according to embodiments of the present invention.

DETAILED DESCRIPTION

Figure 1A:
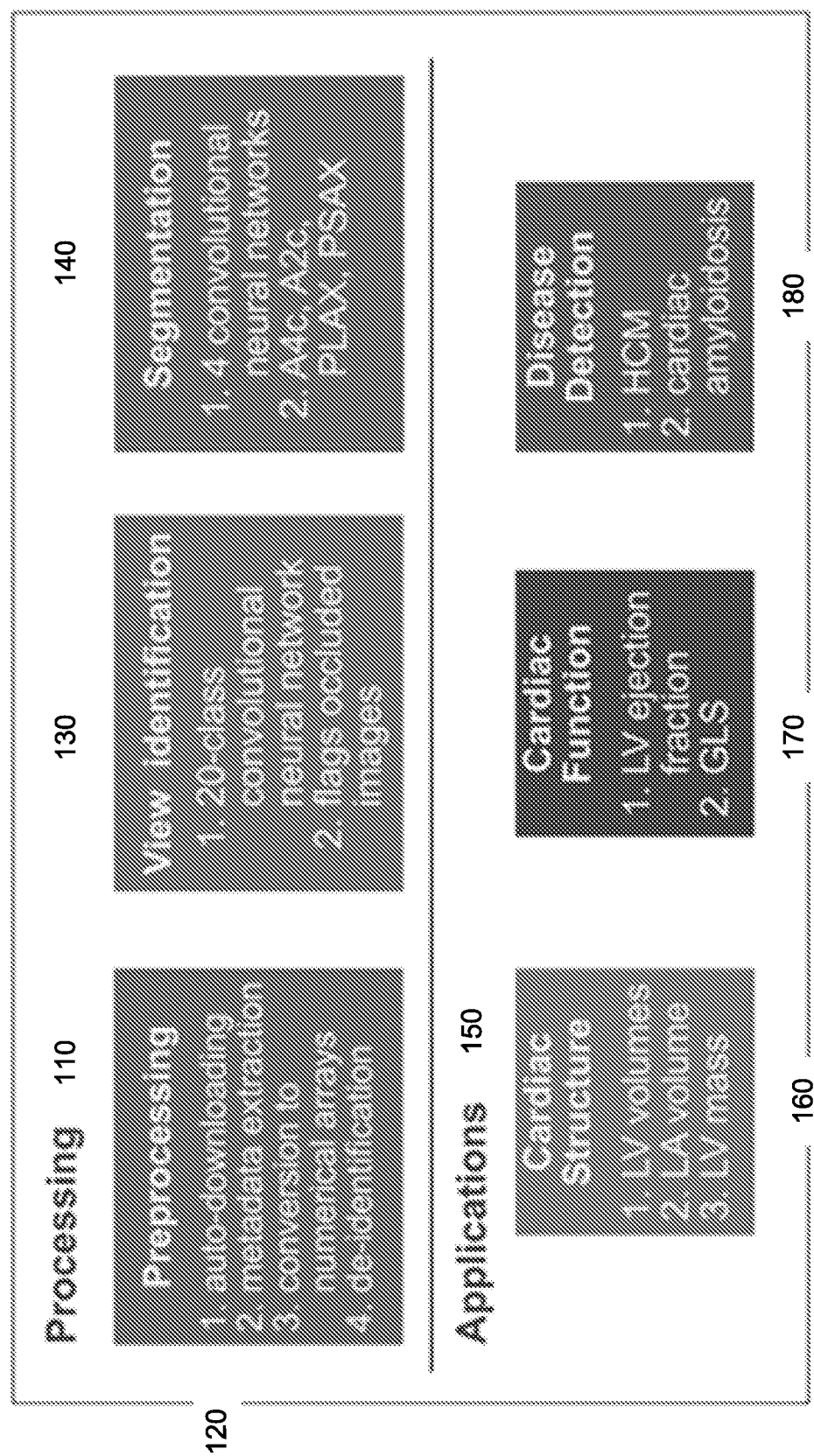
FIGS. 1A and 1B provide an overview of an automated cardiac interpretation pipeline according to embodiments of the present disclosure.

Automated cardiac image interpretation has the potential to transform clinical practice in multiple ways including enabling low-cost serial assessment of cardiac function by non-experts in the primary care and rural setting. Embodiments can use computer vision to build a fully automated, scalable analysis pipeline for echocardiogram (echo) interpretation.

Embodiments can include: 1) preprocessing of complete echo studies; 2) convolutional neural networks (CNN) for view identification, image segmentation, and phasing of the cardiac cycle; 3) quantification of chamber volumes, length, and mass (e.g., left ventricular mass); 4) particle tracking to compute longitudinal strain; and 5) targeted disease detection.

In our work, CNNs accurately identified views (e.g. 99% for apical 4-chamber) and segmented individual cardiac chambers. The resulting cardiac structure measurements agreed with study report values [e.g. median absolute deviations (MAD) of 11.8 g/kg/m$^2$ for left ventricular mass index and 7.7 mL/kg/m$^2$ for left ventricular diastolic volume index, derived from 1319 and 2918 studies, respectively].

The term "index" can refer to a normalization for a given subject, e.g., based on body surface area and/or height and weight of the subject.

In terms of cardiac function, we computed automated ejection fraction and longitudinal strain measurements (within 2 cohorts), which agreed with commercial software-derived values [for ejection fraction, MAD=5.3%. N=3101 studies; for strain, MAD=1.5% (n=197) and 1.6% (n=110)], and demonstrated applicability to serial monitoring of breast cancer patients for trastuzumab cardiotoxicity. Overall, we found that, compared to manual measurements, automated measurements had superior performance across seven internal consistency metrics (e.g. the correlation of left ventricular diastolic volumes with left atrial volumes) with an average increase in the absolute Spearman correlation coefficient of 0.05 (p=0.02).

We also used CNNs to develop disease detection algorithms for hypertrophic cardiomyopathy and cardiac amyloidosis, with C-statistics of 0.93 and 0.84, respectively. We have developed a model for mitral valve prolapse with C-statistic of 0.87. Examples of other diseases to which embodiments may be applied are pulmonary arterial hypertension and heart failure with preserved ejection fraction.

Our pipeline lays the groundwork for using automated interpretation to support point-of-care handheld cardiac ultrasound and large-scale analysis of the millions of echos archived within healthcare systems. Such handheld devices can be connected to a phone or a tablet, as opposed to dedicated components that are much costlier, e.g., as they require a display and user interface for interacting with images.

I. Introduction

An echocardiogram study (echo) is typically a collection of up to 70 videos of the heart taken over multiple cardiac cycles and focusing on different viewpoints, requiring ~45 min by a skilled sonographer. The heart can be visualized from >10 different views—though not truly discrete classes as sonographer can zoom and angle the probe to focus on structures of interest. These are typically unlabeled. Still images are typically included to enable manual measurements. The University of California at San Francisco (UCSF) performs 12,000-15,000 echo studies per year; busier centers perform 30,000-35,000 studies. There are >7,000,000 echos performed annually in the Medicare population alone. There are likely 100,000,000's of archived echos.

Cardiac muscle disease often progresses for years prior to the onset of symptoms. This process, known as cardiac remodeling, can accompany conditions such as valvular disease, hypertension, and diabetes mellitus, and result in pathologic changes to the heart that are difficult to reverse once established. Although early evidence of remodeling is often detectable by imaging and could in principle be tracked longitudinally in a personalized manner, the cost of imaging all individuals with cardiac risk factors would be prohibitive.

Automated image interpretation could enable such monitoring at far lower costs, especially when coupled with inexpensive data acquisition. For echocardiography, one such strategy could involve handheld ultrasound devices used by non-experts at point of care locations (e.g. primary care clinics) and a cloud-based automated interpretation system that assesses cardiac structure and function and compares results to one or more prior studies. Automated image interpretation could also enable surveillance of echo data collected at a given center and could be coupled with statistical models to highlight early evidence of dysfunction or detect rare myocardial diseases. Such an approach could, for example, enable systematic comparison across the tens of millions of echocardiograms completed each year in the Medicare population alone.

Automated image interpretation falls under the discipline of computer vision, which is a branch of machine learning where computers learn to mimic human vision. Although the application of computer vision to medical imaging has been longstanding, recent advances in computer vision algorithms, processing power, and a massive increase in digital labeled data has resulted in a striking improvement in classification performance for several test cases, including retinal and skin disease. Echocardiography, nonetheless, presents challenges beyond these examples. Rather than comprising a single still image, a typical echo study consists of up to 70 videos collected from different viewpoints, and viewpoints are not labeled in each study. Furthermore, measurements can vary from video to video because of intrinsic beat-to-beat variability in cardiac performance as well as variability from the process of approximating a three-dimensional object using two-dimensional cross-sectional images. Given the extent of this variability and the sheer amount of multidimensional information in each study that often goes unused, embodiments can use an automated learning approach to assist human interpretation. In some embodiments, beat-to-beat variability can be addressed by averaging across multiple heart beats, such as every heartbeat.

In this disclosure, we present a fully automated computer vision pipeline for interpretation of cardiac structure, function, and disease detection using a combination of computer vision approaches. We demonstrate the scalability of our approach by analyzing >4000 echo studies and validate our accuracy against commercial vendor packages.

II. Computer Vision Pipeline for Echocardiogram Analysis

A goal was to develop an analytic pipeline for automated analysis of echocardiograms that required no user intervention and thus could be deployed on a high-performance computing cluster or web application. FIG. 1A provides an approach with six steps, falling into processing 110 and applications 150 implemented in a computer system.

At block 120, preprocessing of data files can be performed. The preprocessing can include automated downloading of echo studies in DICOM format, separating videos from still images, extracting metadata (such as frame rate, heart rate), converting them into numerical arrays for matrix computations, and de-identifying images by overwriting patient health information.

At block 130, convolutional neural networks (CNNs) can be used for automatically determining echo views, e.g., apical 4-chamber. The classification of which view a particular set of images corresponds can be used later in the pipeline for identifying a structure in the heart. Section II.A provides additional details on view identification. Example views include apical 2-, 3-, and 4-chamber (A2c, A3c, and A4c), parasternal long axis (PLAX), parasternal short axis at the level of the papillary muscles (PSAX), and the inferior vena cava (IVC).

Embodiments can provide a probability of being in a view, as well as a quality score for that echo (i.e., the video measurement). As an example, a quality score can be determined using (e.g., average or median) a maximum assigned probability of a view across every video in the study. If the best guess for a view still has a low probability, then that measurement might be discarded. An echo can also be discarded for a low quality, which may include the view probability. Some embodiments can provide feedback to a technician if the current echo is of poor quality. This can occur when the current video is being analyzed in real time. For example, an audio, visual, or haptic feedback can be provided to a technician to indicate that a current or recent position of the device is providing images of poor quality, e.g., which cannot be properly classified as a particular view. If the device includes a display screen, an expected location (and possibly orientation) of the device can be displayed to the user, e.g., overlaid on a template image of a person. In various embodiments, the feedback can provide a general alert, which can indicate a problem, or provide specific guidance on how to move the device, e.g., a direction. The direction can be determined based on identifying a best view and providing instructions to the technician of the direction to move the device to reach the predetermined position associated with the identified view.

At block 140, based on the identified views, videos can be routed to specific image segmentation models, e.g., parasternal long axis, parasternal short axis, apical-2, apical-3, and apical 4-chamber, which may be implemented as CNNs. Every view may be only assigned to a single segmentation model. Section II.B provides additional details on image segmentation. In some embodiments, multiple segmentation models can be used. In some implementations, four separate segmentation models can allow delineation of between three and six structures on every image. For example, for the apical 4-chamber view, embodiments can identify the blood pool of the left ventricle, right ventricle, right atrium, left atrium as well as the muscular segment of the left ventricle. The results of the segmentation can then be used for calculations of specific structural and functional parameters in a focused way: such as left atrial volumes or right ventricular strain.

The segmentation can help with views that are not typical, e.g., zoomed views. Some embodiments can subdivide structures to identify what is being viewed. For example, if some structures are partially obscured because the individual who collected the data zoomed in on a certain part of the heart, embodiments can distinguish between those variants where a structure (e.g., left atrium) was cut off versus those where it is complete. Some implementations can provide a probabilistic way of identifying what is being viewed, e.g., each pixel can have a probability of being in different regions (e.g., one of the four chambers or outside of the heart). Such an analysis can cause all or some images of an echo at a particular view to be discarded or only used for certain measurements, e.g., if a certain structure(s) is not visible.

Accordingly, embodiments can sort videos in a broad sense of what the view is, but also what structures are sufficiently visible for use in further measurements. Using separate classes for views with obscured structures (e.g. apical-2 with obscured left atrium) and those with unobscured structures (e.g. apical-2 with unobscured left atrium and ventricle), embodiments can compare the probabilities to determine whether the video should be used to estimate atrial size. For example, if the probability is higher for a class with an obstructed structure, the video can be omitted. As another example, if a sufficient number of pixels (e.g., by comparison to a cutoff value) of an image do not have a probability higher than a probability threshold for corresponding to a particular structure, then that image can be omitted from further analysis involving that heart structure.

At block 160, the output of 140 can be used to derive chamber measurements, including lengths, areas, volumes, and estimates of mass for a particular heart structure, such as left/right ventricles (LV/RV) and left/right atria (LA/RA). The corresponding segmented images can be used to compute standard measurements of cardiac structure, e.g., averaging across multiple cardiac cycles within a video and multiple videos for a given view. Section II.C provides additional details on quantification of chamber structure and function.

At block 170, cardiac function can be measured using the output of 140. As two examples, we generated two commonly used measures of left ventricular function: ejection fraction and longitudinal strain. The function can be determined as an extrapolation from the measurements that are made at different parts of the cardiac cycle. The ejection fraction can be determined as a difference in the volumes at the peak and at the minimum value. It can be computed over multiple cycles, and an average can be taken. Section II.D provides additional details. In various implementations, the segmentation can derive two indices of cardiac function: left ventricular ejection fraction and global longitudinal strain (GLS). We have also derived measures of right ventricular and left atrial strain.

At block 180, view-classified videos can be used to detect disease. As examples, diseases can be diagnosed by combining interpretations across multiple views, including parasternal long-axis, apical-2, apical-3, and apical-4 as well as parasternal short-axis. For example, parasternal long-axis (PLAX) videos can be phased to identify images at the end of cardiac systole and diastole. The phasing identifies which phase an image corresponds. The resulting image pairs (end of two phases) can be used to detect a disease, e.g., characterized by abnormal cardiac thickening, such as hypertrophic cardiomyopathy (HCM) and cardiac amyloidosis. Accordingly, pairs of images of a same view (e.g., PLAX and A4c images) corresponding to same position in a phase (e.g., end-systole and end-diastole) can be phased to detect a disease. For other diseases such as mitral valve prolapse, multiple images directly proceeding and following end-systole may be used. Thus, images at a particular stage of the cardiac cycle can be selected for a particular disease. Section II.E provides additional details for disease detection.

Phasing is usually performed using an EKG, but this requires extra measurements. Instead, embodiments can use the segmentation and structure information over cycles to identify which part (stage/phase) of a cycle a given image corresponds: systole or diastole. Images from a same part of the cycle can be bundled together (or multiple bundles, each for different parts of the cycle) and fed into a classifier to detect different diseases. As examples, different parts of the cycle can correspond to most relaxed or most contracted states. Certain diseases, such as mitral valve prolapse, are best identified using images of certain parts of the cardiac cycle.

To perform phasing, structure measurements can be plotted over time (e.g., internally by the software) as a set of cycles (e.g., as a wave), and points along that curve can define different aspects of the cardiac cycle (e.g., peaks (maximum) and valleys (minimum) of the volume of a particular chamber). For instance, the view identification can provide an input to the segmentation module, so as to identify a chamber accurately, which then allows tracking its size, which then allows selecting a part of the cycle, e.g., where it is the largest or smallest.

Figure 1B:
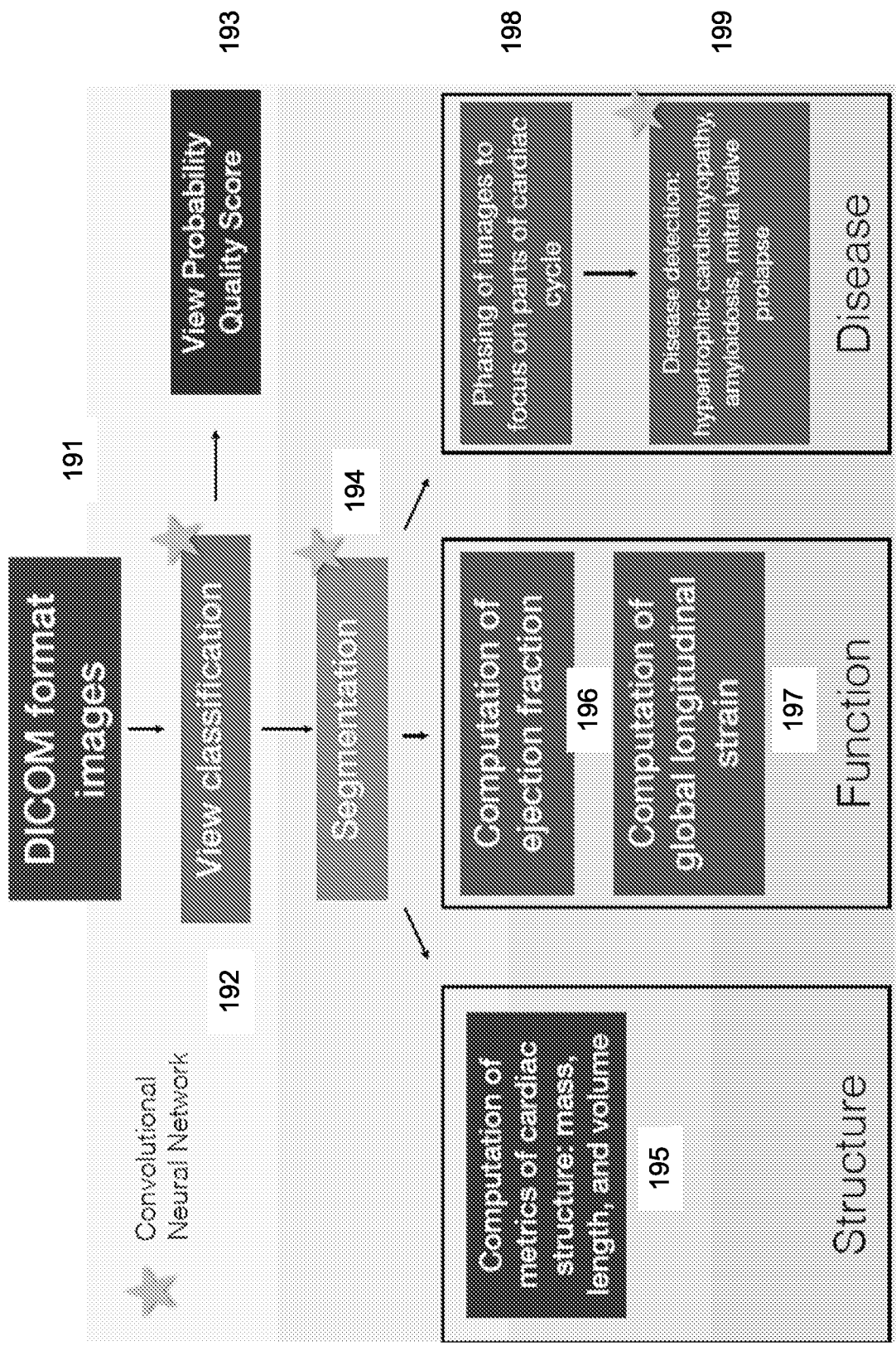

FIG. 1B shows similar steps showing an order of operation and the applications of structure, function, and disease. FIG. 1B shows steps that may use a convolutional neural network. At block 191, images are received (e.g., as DICOM formatted images). At block 192, view classification is performed. The view classification can provide a probability score 193 of an image being in each of a plurality of views. At block 194, segmentation can be performed on the view-classified images. At block 195, metrics of cardiac structure (e.g., mass, length, and volume) can be performed using the segmentation results of the view-classified images. At block 196, an ejection fraction can be computed using the segmentation results of the view-classified images. At block 197, global longitudinal strain can be computed using the segmentation results of the view-classified images. At block 198, images can be phased to identify images corresponding to particular parts of the cardiac cycle. Block 198 may also use information from block 195 to perform the phasing, e.g., using variations in a metric (such as volume, mass, length, etc.) to identify images corresponding to particular positions in a cardiac cycle. At block 199, disease may be detected using the images identified at the particular parts of the cardiac cycle. Example diseases include hypertrophic cardiomyopathy, cardiac amyloidosis, and mitral valve prolapse. Below we elaborate on these steps, both providing technical details of performance as well as clinical applications.

A. Convolutional Neural Networks ("Deep Learning") for View Identification

Typical echo studies consist of up to 70 separate videos representing multiple different viewpoints. For example, several different views are taken with the transducer placed beside the sternum (e.g. parasternal long axis and short axis views), at the cardiac apex (apical views), or below the xiphoid process (subcostal views). Furthermore, with rotation and adjustment of the zoom level of the ultrasound probe, sonographers actively focus on substructures within an image, thus creating many variations of these views. Unfortunately, none of these views are labeled explicitly. Thus, the first learning step involves teaching the machine to recognize individual echo views.

For an initial model, we manually labeled six different views: apical 2-, 3-, and 4-chamber (A2c, A3c, and A4c), parasternal long axis (PLAX), parasternal short axis at the level of the papillary muscles (PSAX), the inferior vena cava (IVC) and labeled all as "others". We next used a multi-layer convolutional neural network to distinguish between the different views.

Such deep learning is a form of machine learning devised to mimic the way the visual system works. The "deep" adjective refers to multiple layers of "neurons", processing nodes tuned to recognize features within an image (or other complex input). The lower layers typically recognize simple features such as edges. The neurons in subsequent layers recognize combinations of simple features and thus each layer provides increasing levels of abstraction. The features in the top layer are typically used in a multiclass logistic regression model (or other classification model), which provides a final probabilistic output for classification.

Figure 2B:
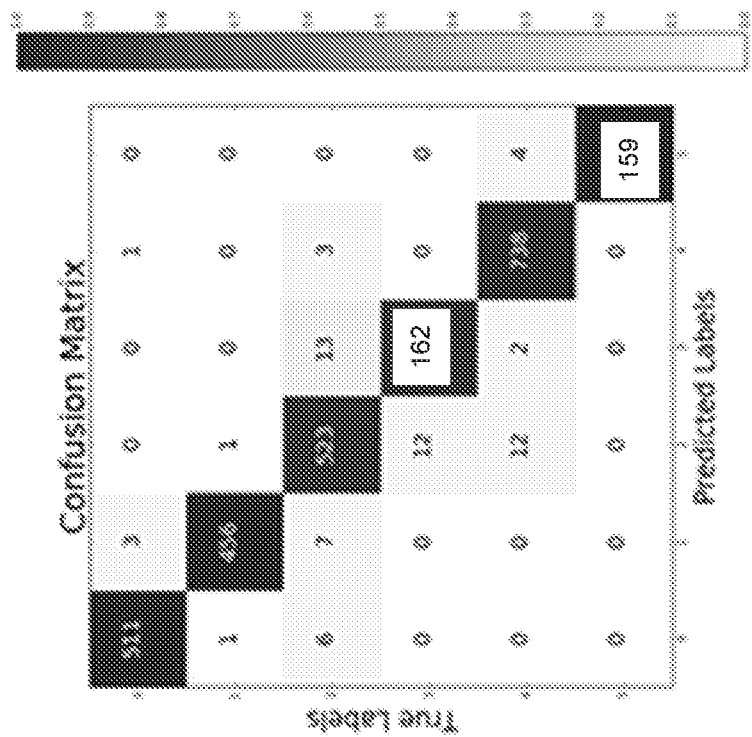
FIGS. 2A and 2B show a convolutional neural network successfully discriminating echo views according to embodiments of the present disclosure.
Figure 2A:
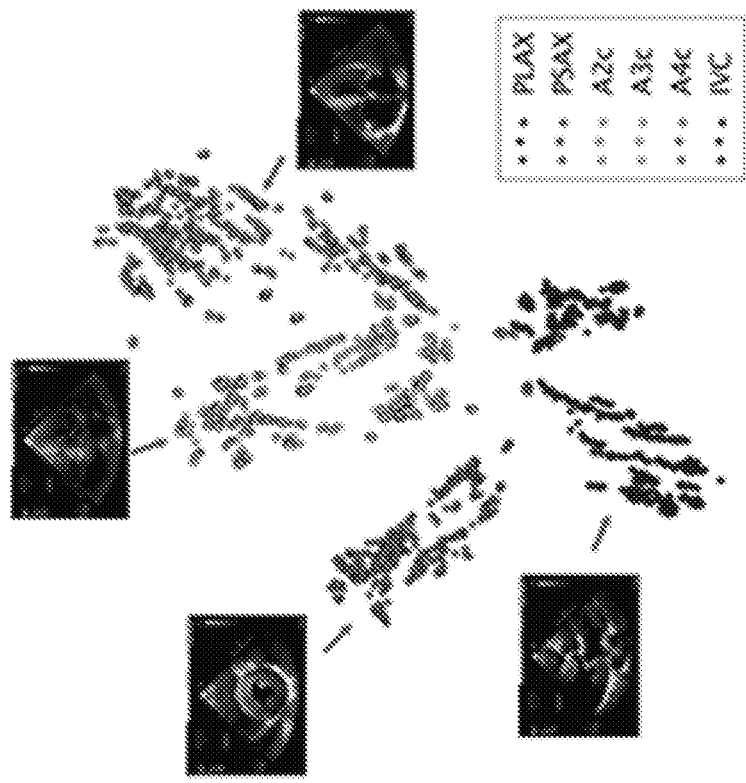

FIGS. 2A and 2B show a convolutional neural network successfully discriminating echo views according to embodiments of the present disclosure. We trained a 13-layer network and found an extremely high level of accuracy for view classification as judged by cross-validation (e.g. 99% for parasternal long axis). FIG. 2A shows t-distributed stochastic neighbor embedding (tSNE) visualization of view classification. tSNE is an algorithm used to visualize high-dimensional data in lower dimensions. It depicts the successful grouping of test images corresponding to six different echocardiographic views. Views are numbered as follows: 0) PLAX; 1) PSAX; 2) A2c; 3) A3c; 4) A4c; 5) IVC. Clustering of the top layer features by tSNE for visualizing high-dimensional data revealed clear separation of the different classes, with intuitive closer groupings of some pairs (e.g. A2c and A3c). Another example of deep learning for viewpoint classification is Gao et al. (X. Gao et al. A fused deep learning architecture for viewpoint classification of echocardiography. Information Fusion 36, pages 103-113, 2017).

FIG. 2B shows a confusion matrix demonstrating successful and unsuccessful view classifications within a test data set. Numbers along the diagonal represent successful classifications while off-diagonal entries are misclassifications. As shown by the confusion matrix, the classification was highly accurate.

We next trained a broader (22-class) network to enable detection of whether certain chambers are only partially visualized, as this would be essential for accurate quantification of cardiac structure and function. For example, identifying A2c views where the left atrium is partially missing (e.g., an occluded class) would enable excluding these videos when quantifying left atrial volumes. As another example, views that include a particular structure, but may be missing completely or partially) another structure, can be used when analyzing the particular structure, as opposed to completely discarding a particular segment of the echo. For subsequent steps, we focused on PLAX, PSAX, A2c, and A4c views as these would be used to derive measures of cardiac structure and function and to develop detection models for specific diseases.

B. CNNs for Image Segmentation

Image segmentation involves identifying the location of objects of interest within an image. For example, one could identify the faces of people in a surveillance camera video or the location of other automobiles on the road in front of a self-driving car. Given that image segmentation represents a critical component of computer vision and robotics, computer scientists have developed multiple different algorithms to carry out this task.

We initially used active appearance models for this task. However, we found that deriving a two-step approach consisting of first deriving a bounding box around the chamber of interest was error-prone. We thus used an approach relying exclusively on CNN-based methods and trained separate models for PLAX, PSAX, A2c, and A4c views, which each localized 3-6 structures (Table 1). For example, for A4c, we segmented the blood pools for both the right and left atria and ventricles, the outer myocardial boundary of the left ventricle, and the epicardial boundary of the whole heart. We found very good performance for our models, with intersection over union (IoU) values ranging from 73 to 92 for all structures of interest (the outer boundary of the entire heart was an outlier).

Figure 3:
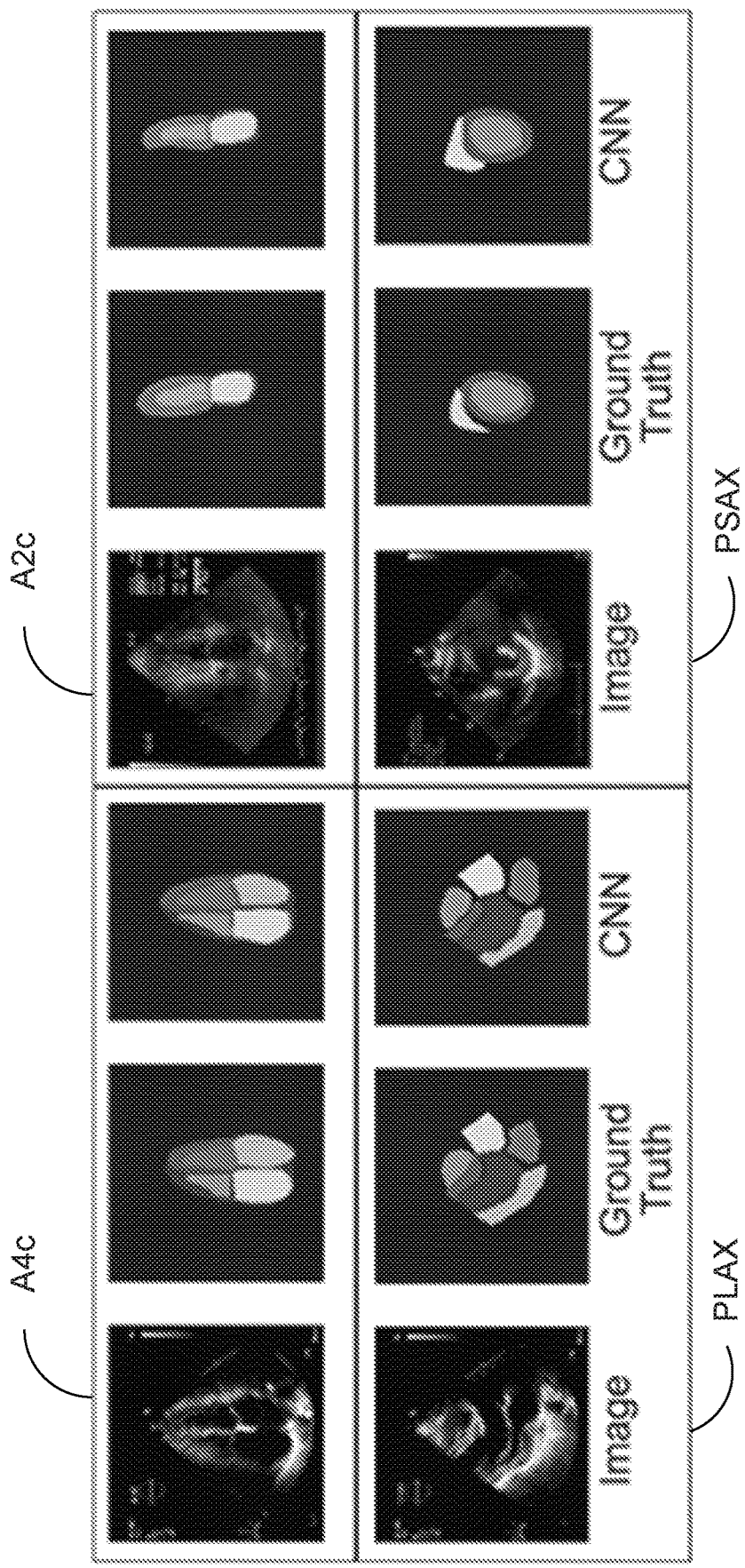
FIG. 3 shows the analysis for different segmentation models corresponding to four different views according to embodiments of the present disclosure.

Table 1 shows results for the U-Net algorithm training CNN models to segment echocardiographic images according to embodiments of the present disclosure. The first column provides the view. The second column provides the number of images tested. The third column identifies the different areas (structures) that are segmented. The final column displays accuracy, as determined by cross-validation, of segmentation of specific structures within images from 4 different echocardiographic views. Segmented regions are depicted in FIG. 3.

TABLE 1

| View | Number of Images Tested | Segmented Area | IOU Accuracy |
| --- | --- | --- | --- |
| Apical 2-Chamber (A2C) | 200 | Left atrium blood pool | 90.6 |
| | | Left ventricle blood pool | 88.1 |
| | | Left ventricle muscle | 72.7 |
| | | Outer cardiac boundary | 55.3 |

TABLE 1-continued

| View | Number of Images Tested | Segmented Area | IOU Accuracy |
|---|---|---|---|
| Apical 4-Chamber (A4c) | 177 | Left atrium blood pool | 91.7 |
| | | Left ventricle blood pool | 89.2 |
| | | Left ventricle muscle | 74.0 |
| | | Right atrium blood pool | 81.2 |
| | | Right ventricle blood pool | 88.0 |
| | | Outer cardiac boundary | 74.0 |
| Parasternal long axis (PLAX) | 104 | Left atrium blood pool | 83.1 |
| | | Right ventricle blood pool | 85 |
| | | Aortic root | 84.7 |
| | | Outer cardiac boundary | 86.8 |
| | | Anterior septum | 76.3 |
| | | Posterior wall | 72.7 |
| Parasternal short axis (PSAX) | 76 | Left ventricle blood pool | 91.9 |
| | | Left ventricle muscle | 79.0 |
| | | Right ventricle blood pool | 78.6 |

FIG. 3 shows the analysis for different segmentation models corresponding to four different views according to embodiments of the present disclosure. Each model can perform a multi-class segmentation for different structures. The models are trained using manually traced training examples (manual traced for an entire video for a view), and then the model is built by performing various distortions or changes to that training data to improve the robustness of the model, e.g., improving accuracy for new images. The images can be modified so that worse images can still be segmented. Each pixel can be identified as being in a structure or not, e.g., as signified by 0 or 1, or have a value in between indicating a probability of being in a structure.

FIG. 3 shows convolutional neural networks successfully segment cardiac chambers. We used the U-net algorithm to derive segmentation models for 4 views: A4c (top left), A2c (top right), PLAX (bottom left) and PSAX at the level of the papillary muscle (bottom right). For each view, the trio of images, from left to right, corresponds to the original image, the manually traced image used in training (Ground Truth), and the automated segmented image (determined as part of the cross-validation process).

The structures can include the blood area and the muscle area. An output can be a probability of each pixel being in one of the structures. In some implementations, different sub-models can be used for different chambers. A structure can be identified using the pixels that have a probability above a threshold. One structure can be an 'other' category that is not of interest.

C. Chamber Structure and Function Quantification

As an independent "real-world" confirmation of segmentation, we derived commonly used measures of cardiac structure and compared our results to thousands of measurements derived from the University of California, San Francisco (UCSF) echocardiography laboratory, which uses a variety of vendor-derived software packages. We downloaded >4000 studies and performed view classification and segmentation, deriving measurements according to standard guidelines. For most studies, we used 6 to 8 videos for each measurement and derived a robust aggregate measure across all the studies, averaging across multiple cardiac cycles. Further details for performing the measurements is provided in section IV.

Figure 4A:
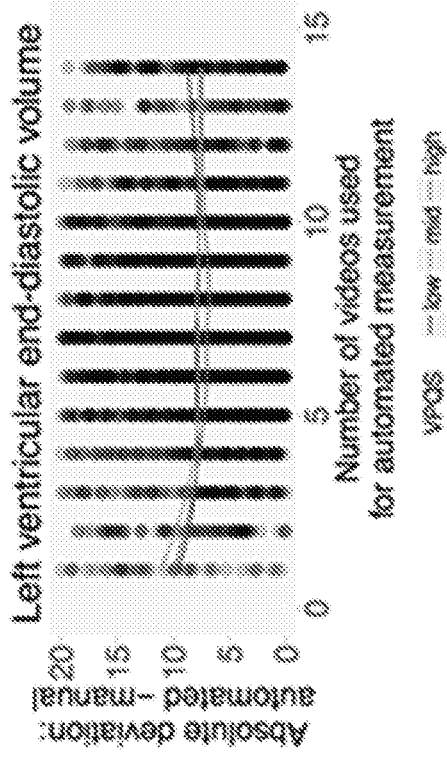
FIGS. 4A-4D show automated segmentation results in accurate cardiac structure measurements in "real-world" conditions according to embodiments of the present disclosure.

FIGS. 4A-4D show automated segmentation results in accurate cardiac structure measurements in "real-world" conditions according to embodiments of the present disclosure. FIG. 4A shows a Bland-Altman plot comparing automated and manual (derived during standard clinical workflow) measurements for indexed left ventricular end diastolic volume (LVEDVI) from 2915 echo studies. Orange, red, and blue dashed lines delineate the central 50%, 75% and 95% of patients, as judged by difference between automated and manual measurements. The solid gray line indicates the median. The horizontal axis provides the mean of the two measurements: automated and manual.

Figure 4B:
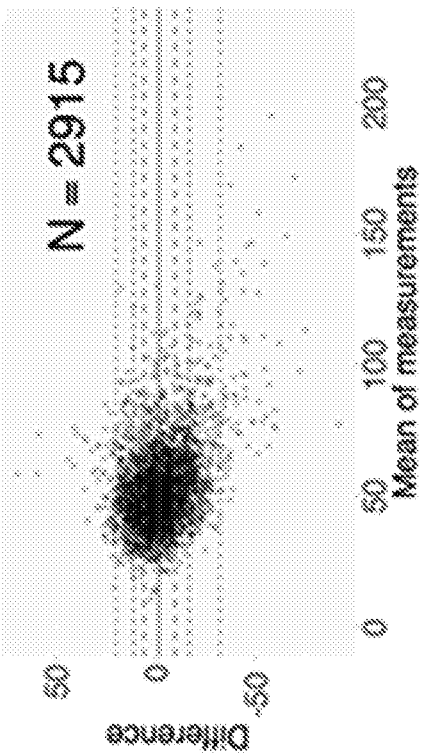

FIG. 4B shows a scatter plot relating the absolute deviation between automated-manual measurements for LVEDVI and the number of videos used in the estimation. A separate loess fit is made for each of 3 tertiles of "study quality score" as judged by the average of the probability of view assignment across the study made by the CNN in FIG. 2. All measurements made with greater than 15 studies were binned together.

As described, the measurements of cardiac structure can rely on aggregation across multiple cardiac cycles within a video and across multiple videos of the same cardiac chamber. We explored to what extent each additional study contributes to the agreement between automated and measured values by fitting a linear regression model to the absolute deviation. We also generated a predictor for "study quality" based on the confidence with which views could be classified by the CNN described above. Specifically, we took a median of the probability of the assigned class for all videos in the study, generating a value between 0 and 1 and termed it a "view probability quality score" or VPQS. We found that for LVEDVI, each 0.1 increase in VPQS reduced the absolute deviation by 2.0 mL/kg/m$^2$ (p=8×10$^{-10}$) and that each additional study used (up to 15) modestly reduced the absolute deviation by 0.02 mL/kg/m$^2$ (p=0.02) (FIG. 4B).

Figure 4C:
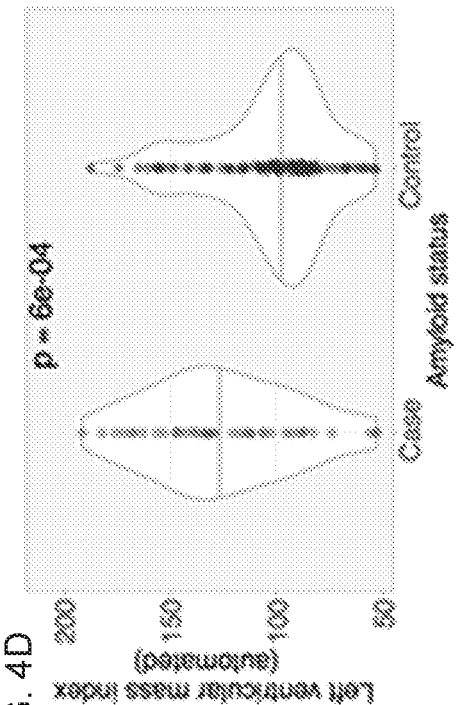

FIG. 4C shows violin plots illustrating that automated measurements reveal a difference in left atrial volumes between hypertrophic cardiomyopathy (HCM) patients and matched controls. A primary difference is in the median values (horizontal lines) between the two distributions. Changes in cardiac structure can also be useful in risk models for various diseases. For example, left atrial enlargement is a predictor for sudden cardiac death in HCM, a disease of cardiac thickening, and one could envisage an automated standardized system to compute such measures for HCM patients. As expected, we found clear differences in left atrial volumes between HCM cases and matched controls using our automated measurements (40 vs. 25 mL/kg/m$^2$, p<2.2×10$^{-16}$, FIG. 4C). The p number is determined between the two distributions using the Mann-Whitney test.

Figure 4D:
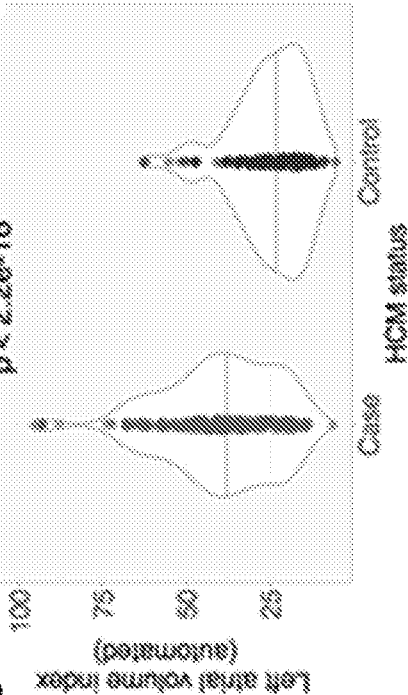

FIG. 4D shows a difference in left ventricular mass between cardiac amyloidosis patients and matched controls. Similarly, for cardiac amyloidosis, a condition described below, we found markedly increased left ventricular mass (125 vs 103 mg/kg/m$^2$, p=0.0006, FIG. 4D). A difference in the median between the two statuses can be readily seen, as is also evidenced by the p number.

Accordingly, embodiments can make all of the common measurements for B-mode echo, a typical 2D visualization. Measurements can be averaged across every cardiac cycle of every relevant video. As to the speed, we processed ~¼ of UCSF's annual echo output in 2 weeks.

We compared our results with values derived from the routine clinical workflow (not all measurements were recorded for every study) and found excellent agreement for body-surface area indexed left atrial volume (LAVOLI) and three left ventricular measures: (indexed) left ventricular mass (LVMI), left ventricular end diastolic volumes (LVEDVI) and left ventricular end systolic volume (LVESVI), (Table 2, FIG. 4A).

TABLE 2

| Metric (units described in table legend) | Number of Echo Studies Used for Comparison | Median Value (IQR) | Absolute Deviation: Automated vs. Manual | | |
|---|---|---|---|---|---|
| | | | 50% | 75% | 95% |
| Left atrial volume index | 1452 | 27.7 (22.0-36.7) | 4.7 | 8.7 | 16.9 |
| Left ventricular diastolic volume index | 2915 | 51.8 (41.8-63.8) | 7.7 | 14.0 | 26.1 |
| Left ventricular systolic volume index | 2910 | 18.8 (14.3-24.9) | 4.7 | 8.5 | 16.9 |
| Left ventricular mass index | 1319 | 81.0 (68.2-100.2) | 11.5 | 19.8 | 43.0 |
| Left ventricular ejection fraction | 3101 | 64.0 (57.9-68.6) | 5.3 | 9.9 | 19.1 |
| Global longitudinal strain | 197 | 18.0 (17.0-20.0) | 1.5 | 2.6 | 5.0 |
| Global longitudinal strain (John Hopkins PKD cohort) | 110 | 18.0 (16.0-20.0) | 1.6 | 2.8 | 5.4 |

Table 2 shows a comparison between fully automated and manual measurements derived from 2-dimensional echocardiography. Absolute deviations are reported as percentiles. For each metric, 50%, 75%, and 95% of studies have an absolute deviation between automated and manual measurements that is less than the indicated value. Units are mL/kg/m2 for left atrial and left ventricular volumes and g/kg/m2 for left ventricular mass. Ejection fraction and global longitudinal strain are dimensionless. IQR=interquartile range. Accordingly, the results show good accuracy between the automated and manual measurements.

As an independent measure of performance we assessed how well each method (i.e. automated vs. manual) could identify associations between different metrics. For example, it is known that the left atrium enlarges in patients with increased ventricular volume and mass, presumably reflecting increased ventricular pressures transmitted to the atria. We found a stronger association by automated compared to manual estimation for LAVOLI vs. LVEDVI [$\rho$=0.50 (automated vs. automated) vs. 0.42 (manual vs. manual), N=1366] and LAVOLI vs. LVESVI [$\rho$=0.47 (automated vs. automated) vs. 0.38 (manual vs. manual), N=1366], though a slightly weaker association for LAVOLI vs. LVMI [$\rho$=0.47 (automated vs. automated) vs. 0.50 (manual vs. manual), N=825]. We also found a slightly stronger inverse relationship between automated LAVOLI and left ventricular ejection fraction [$\rho$=−0.18 (automated vs. automated) vs. −0.15 (manual vs. manual), N=1367], which is a measure of function. We describe a non-parametric statistical test in a section IV.G to assess the likelihood that these differences in measures of internal consistency arise by chance.

Table 3 shows a comparison of the association of manual and automated values.

TABLE 3

| Internal Comparison | UCSF (manual) | EchoCV (automated) |
|---|---|---|
| GLS vs. EF | 0.47 | 0.48 |
| LAVOLI vs. LVEDVI | 0.42 | 0.50 |
| LAVOLI vs. LVESVI | 0.38 | 0.47 |
| LAVOLI vs. LVEF | −0.15 | −0.18 |
| GLS vs. LVEDVI | −0.14 | −0.19 |
| GLS vs. LVESVI | −0.31 | −0.40 |
| LAVOLI vs. LVMI | 0.50 | 0.47 |

Figure 5A:
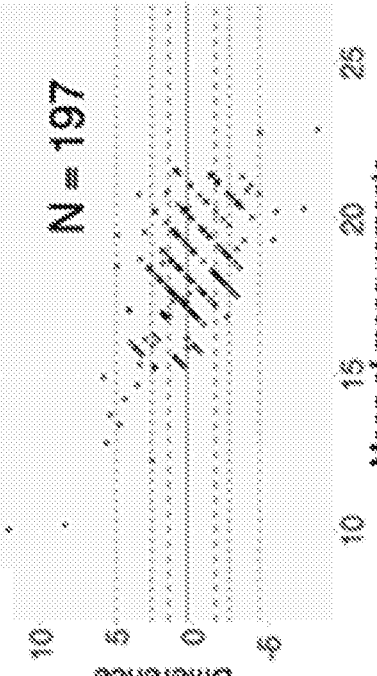
FIGS. 5A-5D shows an automated computer vision pipeline accurately assessing cardiac function according to embodiments of the present disclosure.

D. Assessing Cardiac Function by Ejection Fraction and Global Longitudinal Strain In addition to assessing the structure of the heart, 2D echocardiography provides estimates of cardiac function. The most commonly used metric (ejection fraction) can be readily computed from segmentation of the left ventricle during end diastole and end systole. In keeping with our performance on individual left ventricular volume metrics, we found a strong if not stronger performance for ejection fraction (EF), with a MAD of 5.3% (median EF 64%, N=3101, FIG. 5A).

Along with EF, longitudinal strain is an increasingly popular method to assess the longitudinal function of the heart. It is a sensitive measure of cardiac dysfunction and is tolerant of errors in mapping of the endocardial border, whereas ejection fraction estimates depend on perfect delineation of this boundary. Although commercial packages to measure strain have been available for many years, they invariably require some user intervention and thus cannot be implemented in a scalable, fully automated pipeline. Furthermore, the black-box nature of these packages has made it difficult to interpret how the measurement is made and what limitations there may be.

Accordingly, we developed our own technique for strain estimation, which expanded on a previously published approach (D. Rappaport et al., Assessment of myocardial regional strain and strain rate by tissue tracking in b-mode echocardiograms. Ultrasound in Medicine & Biology 32, pages 1181-1192, 2006). Some embodiments can track echogenic particles from frame to frame to estimate velocities of particles across the length of the ventricle. Fitting can be performed of this variation in particle velocity with position permitted estimates of myocardial velocity, strain rate, and strain.

Figure 5B:
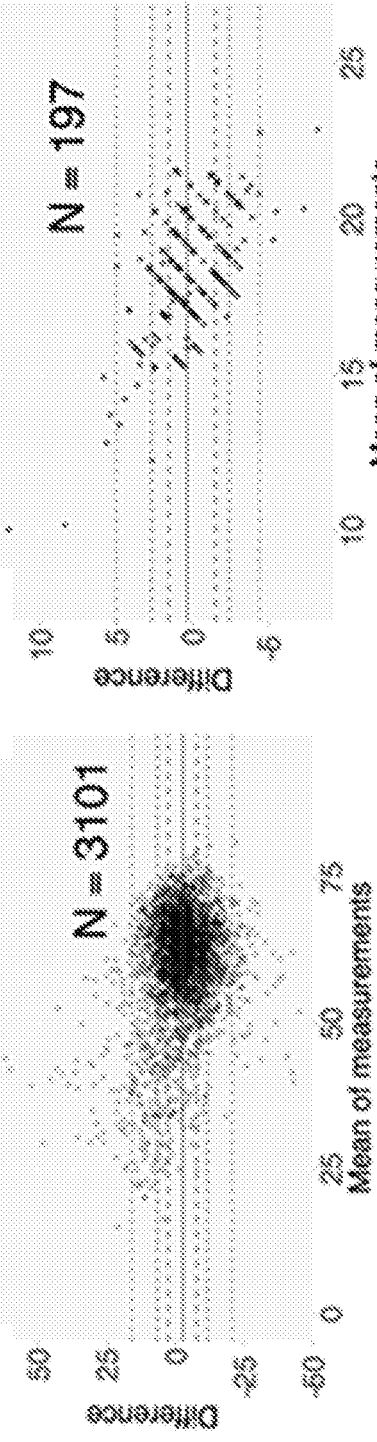

FIGS. 5A-5D shows an automated computer vision pipeline accurately assessing cardiac function according to embodiments of the present disclosure. Bland-Altman plot comparing automated and manual ejection fraction estimates for 3101 individual echo studies (FIG. 5A) and global longitudinal strain (GLS) for 197 echo studies (FIG. 5B). Delimiting lines are as in FIG. 4A.

Figure 5C:
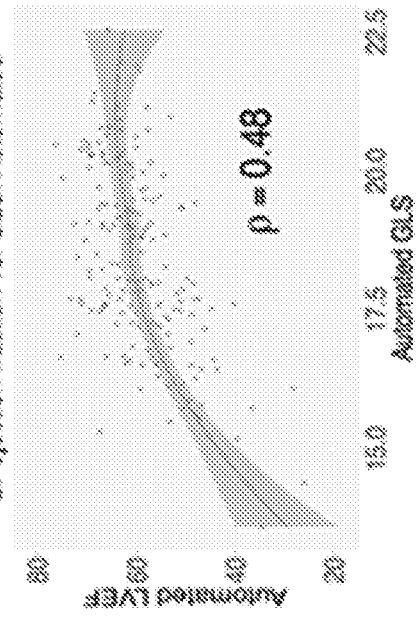
Figure 5D:
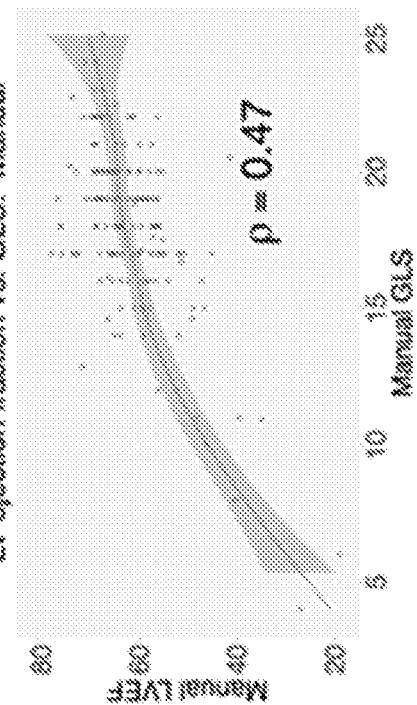

FIGS. 5C and 5D shows scatter plots depicting agreement between ejection fraction and GLS for manual and automated measurements (N=175). Spearman correlation coefficient is shown. A loess fit with standard error is depicted.

As an additional evaluation of our accuracy, we looked at concordance between two measures of LV function across 174 studies: EF and GLS (FIGS. 5C and 5D). We found that the agreement between automated EF and automated GLS ($\rho$=0.48) was nominally better than that of manual EF vs. manual GLS values ($\rho$=0.47). We also analyzed the GLS-LVEDVI association, and found stronger agreement for values generated by automation [$\rho$=−0.19 (automated vs. automated) vs. −0.14 (manual vs. manual), N=174] and even stronger agreement in GLS-LVESVI values for automation

[ρ=−0.40 (automated vs. automated) vs. −0.31 (manual vs. manual), N=174]. Overall, across our seven metrics of internal consistency, we found that our automated values were superior to those found from manual measurements (absolute average increase in Spearman coefficient=0.05, IQR 0.03-0.06, p=0.0198, bootstrap with 10,000 iterations).

1. Comparison to Commercial Packages

We compared our results to measurements based on commercial vendor packages (FIGS. 4A-4D), and found excellent agreement at the patient level (MAD=1.5%, N=197, Table 2 and FIG. 5B). Regarding the comparison with commercial vendor derived measurements, an echo database including measurements for previous studies was used. For downloaded studies, we extracted measurements corresponding to left ventricular and atrial volumes, ejection fraction, mass, and global longitudinal strain. For strain, we also used echo studies collected from a second cohort of patients with polycystic kidney disease. We used embodiments described herein and results were generated blinded to the manual values, which were computed independently by AQ and ML using the TOMTEC (Munich, Germany) cardiac measurement software package.

Figure 6:
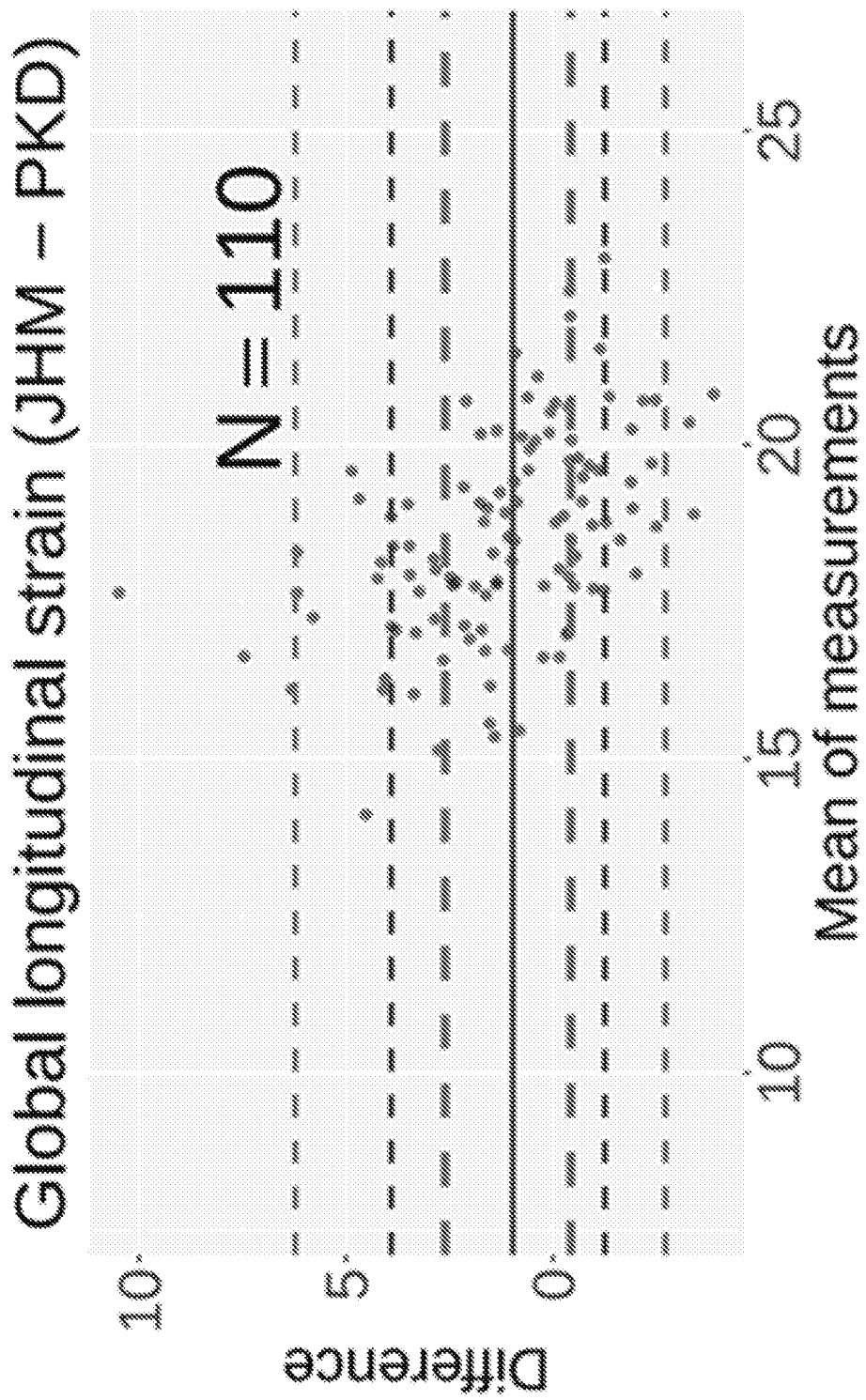
FIG. 6 shows a Bland-Altman plot as in FIG. 5B for 110 studies from a polycystic kidney disease cohort (PKD) according to embodiments of the present disclosure.

Given the modest number of studies used to evaluate strain estimation compared with other metrics, we analyzed a second cohort of 110 patients from a second institution, and saw nearly identical agreement between automated and manual values using TOMTEC (MAD=1.6%, Table 2 and FIG. 6).

FIG. 6 shows a Bland-Altman plot as in FIG. 5B for 110 studies from a polycystic kidney disease cohort (PKD) according to embodiments of the present disclosure. Automated measurements were made blinded to manual measurements.

2. Patient Trajectories of Strain During Treatment

Patient trajectories were also analyzed. Patient trajectories were mapped during Trastuzumab/Pertuzumab treatment.

As described in the introduction, a motivation is to facilitate early, low-cost detection of cardiac dysfunction in asymptomatic individuals to motivate initiation or intensification of therapy. Given our ability to estimate longitudinal strain accurately, we hypothesized that we should be able to use our analytic pipeline to generate quantitative patient trajectories for breast cancer patients treated with cardiotoxic agents. We identified 152 patients treated with trastuzumab or pertuzumab (antibody inhibitors of the Her2 protein), which are known to cause cardiotoxicity in a subset of patients. We downloaded 1047 echo studies from these patients and processed these through our pipeline. We generated automated plots of strain trajectories, overlaid chemotherapy usage and reported ejection fractions onto our visualization.

Figure 7B:
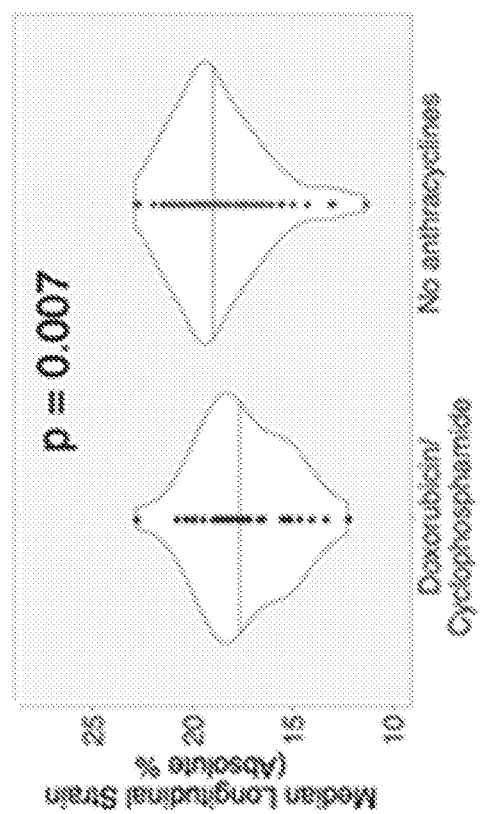
FIGS. 7A and 7B show that automated strain measurements enable quantitative patient trajectories of breast cancer patients treated with cardiotoxic chemotherapies according to embodiments of the present disclosure.
Figure 7A:
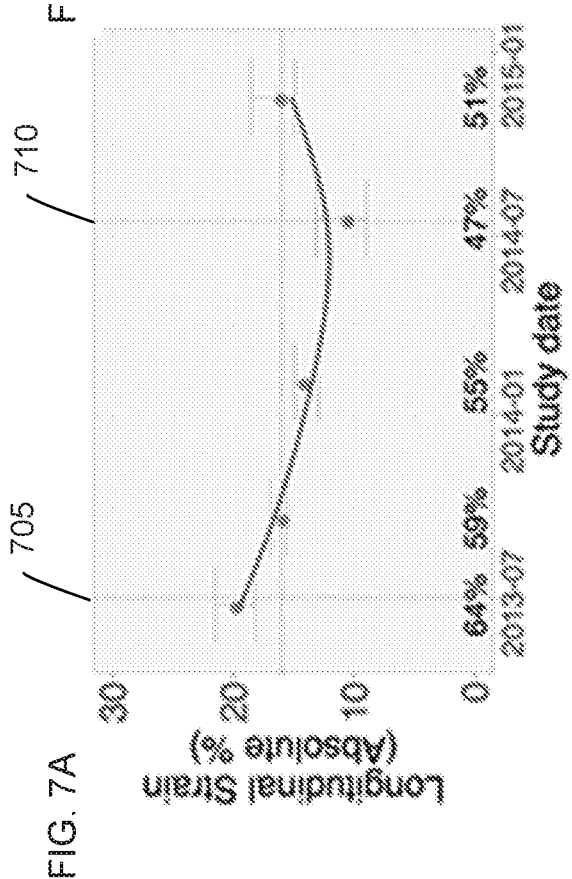

FIGS. 7A and 7B show that automated strain measurements enable quantitative patient trajectories of breast cancer patients treated with cardiotoxic chemotherapies according to embodiments of the present disclosure. Automated strain values were computed for 9421 (apical) videos of 152 breast cancer patients undergoing serial echo monitoring during chemotherapy. Individual plots were generated for each patient.

FIG. 7A shows a plot for a 58 year old woman receiving trastuzumab therapy only. Each colored dot represents an individual echo study. A smoothing spline was fit to the data. Ejection fractions in the published echo report are shown. Vertical blue dashed lines 705 and 710 represent initiation and cessation of trastuzumab therapy. A horizontal dashed line at longitudinal strain of 16% indicates a commonly used threshold for abnormal strain. Accordingly, the automated technique for measuring strain is able to detect the abnormal decrease below 16% that is caused by the treatment.

We observed a breadth of patient trajectories. FIG. 7A reveals an illustrative example, depicting the patient 58-year-old breast cancer patient with Type 2 diabetes mellitus and hyperlipidemia who experienced cardiac dysfunction that improved after cessation of trastuzumab, although the final strain values remains at the lower limit of normal. Such plots (with accompanying statistics) could be generated by a cloud-based interpretation system that stores prior estimates, thus allowing depiction of longitudinal trends.

FIG. 7B shows violin plots illustrating automated strain measurements that confirm the more severe toxicity that occurs when combining trastuzumab/pertuzumab with anthracyclines. The violin plots show median longitudinal strain values for patients pretreated (red) or not pretreated (blue) with neo-adjuvant doxorubicin/cyclophosphamide prior to therapy with trastuzumab (and/or pertuzumab). The combined treatment shows a lower average strain than with no anthracyclines.

Accordingly, to further validate our approach, we also compared average longitudinal strain values in patients who did or did not receive doxorubicin-cyclophosphamide neo-adjuvant therapy prior to receiving trastuzumab/pertuzumab. Consistent with prior results, pretreatment with anthracyclines worsened cardiac function, as represented by lower median (19.7 vs 21.1%, p=0.01) and nadir (16.2 vs. 17.8%, p=0.02) absolute strain values (FIG. 7B).

Regarding the analysis of serial echocardiograms from Trastuzumab- and Pertuzumab-treated patients, patients who received trastuzumab or pertuzumab for adjuvant or metastatic disease or received a screening echocardiogram between 2011 and 2015 were identified using the UCSF pharmacy and echocardiogram databases. Patients with a transthoracic echocardiogram at baseline, early in therapy (<5 months, mean 3.0 months), and at 12 months were included in the cohort (n=152, mean age 54.3 years, all female). Ejection fraction values were extracted from the echocardiogram reports. Patient demographics, co-morbidities, current medications, and oncological history were obtained from chart review. Plots of variation of longitudinal strain with time were generated using the ggplot2 package in R. In addition to plotting strain values, we generated a smoothing spline curve using the smooth.spline function in R.

E. Models for Disease Detection

In addition to quantifying cardiac structure and function, embodiments can automate detection of rare diseases, which may benefit from early recognition and specialized treatment programs. We focused on two diseases of abnormal cardiac thickening: hypertrophic cardiomyopathy (HCM) and cardiac amyloidosis.

HCM, which affects 0.2% of the population, is characterized by cardiomyocyte hypertrophy and disarray and myocardial fibrosis. It can be associated with syncope, atrial and ventricular arrhythmias, heart failure, and sudden cardiac death. Once physicians recognize HCM, they can implement preventive measures, including avoidance of high intensity exercise and implantation of a cardiac defibrillator. Moreover, given that the first presentation of the disease can be sudden cardiac death, including in young athletes, early diagnosis can motivate physicians to screen relatives. HCM can result in unstable heart rhythms, heart failure, and stroke. Management involves behavioral changes, medication, and preventive implantation of a defibrillator.

Using a cohort of HCM patients (with varying patterns of left ventricular thickening) and technically matched controls, we trained a multi-layer CNN model to detect HCM using PLAX- and A4c-view videos. Because the heart changes appearance at different stages of the cardiac cycle, we first phased images using the results of cardiac segmentation, and selected a pair of images, one at end-diastole and one at end-systole, when the left ventricle is at its peak and minimum area, respectively. In other embodiments, the right ventricle can be used, or other heart structure mentioned herein. Other pairs or clusters of images can also be used, such as a group of five images preceding and following end-systole for mitral valve prolapse.

The resulting model could detect HCM with a C-statistic (Area Under the Receiving Operating Characteristic Curve or AUROC) of 0.93. To explore possible features being recognized by the model, we plotted the (logit-transformed) probabilities of disease in cases against left atrial volume and left ventricular mass: two features associated with the disease process (FIGS. 4C and 4D). Cases with higher predicted probability of disease had larger left atria ($\rho$=0.41, Spearman correlation coefficient) and larger left ventricular mass ($\rho$=0.38). As examples, the left ventricular mass can increase with disease; the left ventricular function can diminish with disease, and the left atrial volume can increase with disease. The model can use the pixels assigned (e.g., based on probability) to a heart structure in each of the images as features that are input to the CNN model. The pixels values can be signal intensities. In some implementations, determined properties of one or more structure can also be used as features input to the model, e.g., mass, length, or volume.

We next developed a model to recognize cardiac amyloidosis, a morphologically similar yet etiologically different disease. Cardiac amyloidosis arises from the deposition of misfolded proteins within the myocardium, and can result in heart failure, bradyarrhythmias, and sudden cardiac death. Early recognition of cardiac amyloidosis can result in implementation of therapies including treatment of underlying plasma cell dyscrasias such as multiple myeloma (when the deposited proteins are immunoglobulins) or to target production of the transthyretin protein, which accumulates in other forms of the disease. Cardiac amyloidosis can be diagnosed with confidence using cardiac biopsy or specialized imaging protocols using nuclear imaging or magnetic resonance imaging, but such specialized techniques are costly, not widely available, and thus unlikely to be deployed in many clinical settings. Using amyloid cases and matched controls, we trained a model to cardiac amyloidosis and again found excellent performance, with a C-statistic of 0.84. Similar to HCM, we found that cases with higher predicted probability of amyloid had larger left ventricular mass ($\rho$=0.46) but did not have increased left atrial volumes ($\rho$=−0.10).

FIGS. 8A-8D show CNNs enabling detection of abnormal myocardial diseases according to embodiments of the present disclosure. Receiver operating characteristic curves are shown for hypertrophic cardiomyopathy (FIG. 8A) and cardiac amyloid (FIG. 8B) detection. In each case, separate CNN models were trained using hundreds of pairs of PLAX and A4c-view images for affected and unaffected individuals. A pair of images consisted of one image at end-systole and one at end diastole, where phasing was performed using estimates of the left ventricular area. Other structure values may also be used besides the left ventricular area including a direct classification of end-systole and end-diastole from images, which can make use of the differential movement of valves that define these phases of the cycle.

Figure 8B:
FIGS. 8A-8D show CNNs enabling detection of abnormal myocardial diseases according to embodiments of the present disclosure.
Figure 8A:
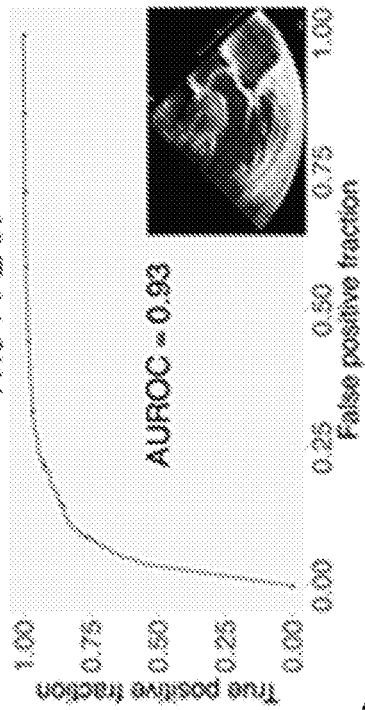
Figure 8D:
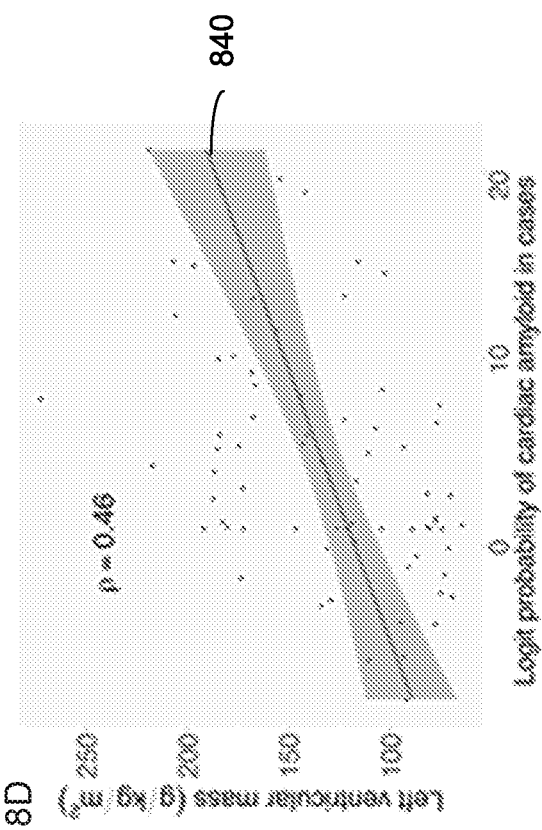
Figure 8C:
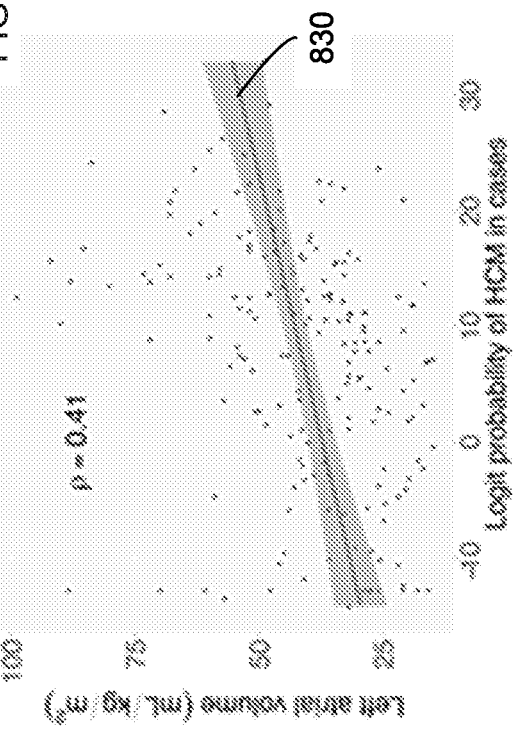

Performance was assessed by cross-validation. Four independent cross validation runs were performed and the test results averaged for each image-pair, and then a median taken across the entire study. Finally, the A4c and PLAX probabilities were averaged. For FIGS. 8C and 8D, within cases, CNN probabilities of disease were correlated with known features of the disease process (FIGS. 4C and 4D). FIG. 8C shows a relationship between probability (logit-transformed) of HCM and left atrial volume with Spearman correlation coefficient indicated. FIG. 8D shows a relationship of probability of amyloid with left ventricular mass. Blue lines 830 and 840 indicate linear regression fit with 95% confidence interval indicated by grey shaded area.

A model was also developed to detect Mitral Valve Prolapse (MVP), using a stack of images at end-systole.

Figure 9:
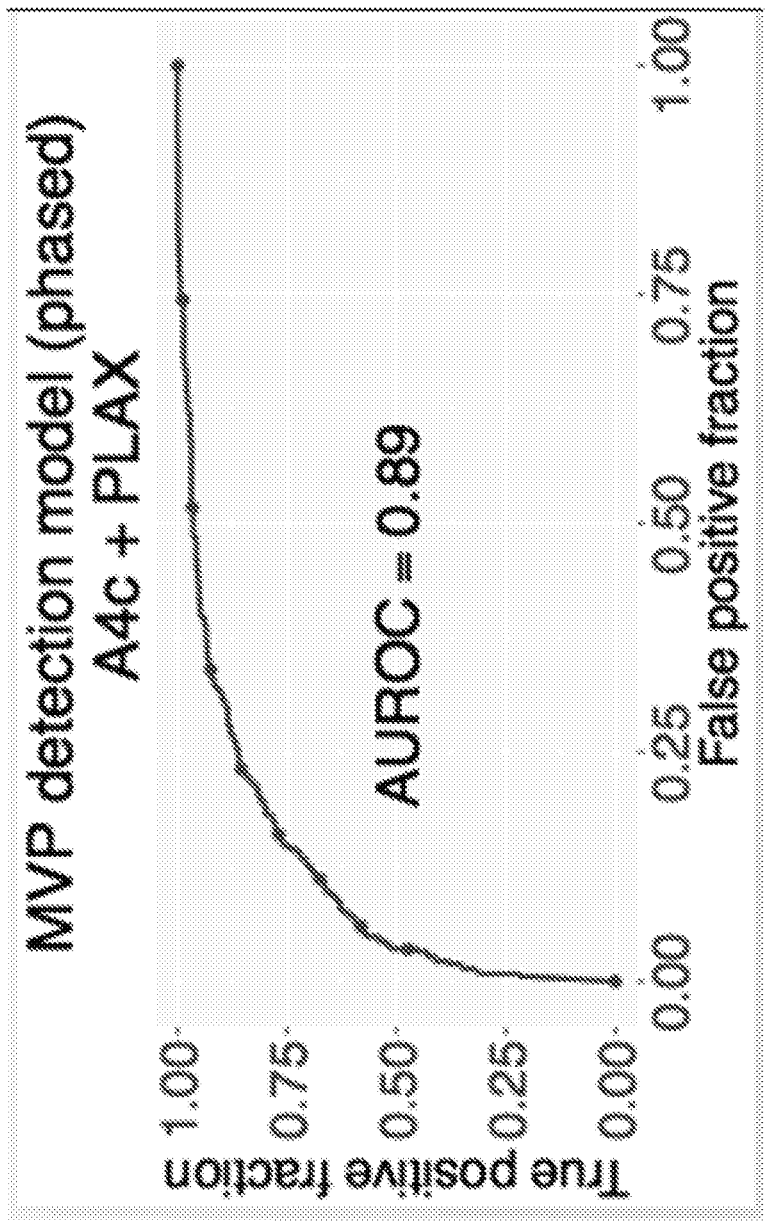
FIG. 9 shows a receiver operating characteristic curves for Mitral Valve Prolapse (MVP) detection according to embodiments of the present disclosure.

FIG. 9 shows a receiver operating characteristic curves for Mitral Valve Prolapse (MVP) detection. MVP is a disease characterized by abnormal myxomatous thickening of the valve leaflets. It is seen in 1% of the population, and can progress to severe valve disease and is sometimes seen with arrhythmia and sudden death.

III. Discussion

We achieved our primary objective, namely to construct an end-to-end automated pipeline for assessment of left ventricular structure, function, and disease detection. This pipeline is fully scalable, as evidenced by our analysis of over 4000 echo studies for this manuscript on a 10-node compute cluster all in a period of less than two weeks. Its modular nature provides multiple points for quality assessment and enables parallel improvement on multiple fronts.

Example improvements provided by this work are the application of CNNs to segment echo images, the development of an empirically validated automated quality score (e.g., VPQS) for studies, the automation of common 2D measurements, the validation of automated values against measurements from thousands of studies, and the creation of a complete pipeline that can be deployed on the web. More training data may be used for improved performance, although it is remarkable to note how few images (<200) were used to train each of our segmentation models.

Embodiments can benefit from averaging across multiple measurements, and we demonstrate the utility of multiple studies in improving concordance between manual and automated measurements. Our results also show benefits from building more redundancy into their acquisition of echo images for using an automated computer vision pipeline for study interpretation. In particular, there is typically only 1 PSAX video available to compute left ventricular mass.

Encouragingly, our assessment of internal consistency—i.e. correlating different metrics such as left atrial and ventricular volumes—indicated that our measurements were better than the typical clinical laboratory values. The ability to average across multiple measurements contributes to the improvement, a feat that would be essentially not possible for humans forced to trace dozens of images by hand.

Some embodiments can be used towards augmenting clinical practice rather than replacing current approaches. For example, measurements may be taken when patients are asymptomatic but at risk of cardiac dysfunction, with quantitative comparisons made to prior studies to obtain personalized longitudinal trajectories. Such an approach can shift evaluation to the primary care setting, with data collected by non-experts—and the resulting initiation and tailoring of care would hopefully reduce the alarming increase in heart failure incidence that has taken place in recent decades. A similar approach can be taken with point-of-care ultrasound at oncology infusion centers—both reducing the cost and increasing the timeliness of diagnoses of cardiotoxicity. In anticipation of such an eventuality, we deliberately avoided using any ECG information in our pipeline to accommodate analysis of data from low-cost portable handheld ultrasound devices.

Moreover, we have found that the combination of automated preprocessing and the ability to identify individual echo views using deep learning allows rapid accrual of training data for specific tasks, such as training models for the detection of mitral valve prolapse or pulmonary arterial hypertension. Embodiments can have a broad clinical impact by 1) introducing relatively low-cost quantitative metrics into clinical practice; 2) extracting knowledge from the millions of archived echos available in echo laboratories; and 3) enabling causal insights that require systematic longitudinal tracking of patients.

IV. Materials and Methods

The following section provide examples details for implementing various embodiments of the present disclosure.

A. Preprocessing

In some embodiments, auto-downloading of DICOM format echo studies from the Syngo client was performed. The studies stored within our echo database (Syngo, Siemens Healthcare) were in a proprietary format that could not be used for image analysis. To avoid manual download of the thousands of studies used for this project, we wrote scripts using AutoIt software (www.autoitscript.com/site/autoit/) to mimic human interaction with the web-based client. This enabled downloading individual studies in Digital Imaging and Communications in Medicine (DICOM) format specified by date or medical record number at a rate of approximately 1 study per 2 minutes.

Typical echo studies consist of a combination of 80-120 still images and videos. The still images are usually used for manual measurements and thus our primary interest was in the videos. We first used the pydicom Python library to count the number of frames within each file thus enabling separation of still images from videos. We next used the gdmconv utility from the Grassroots DICOM Library (GDCM) to convert compressed DICOM format videos into a raw DICOM format. This allowed use of the pvdicom library for conversion of DICOM videos into numerical arrays. In doing so, we also "blacked out" the identifying patient information on the videos by setting the corresponding pixel intensities to minimal intensity. Numerical arrays were compressed for subsequent use. A subset of these were converted into Audio Video Interleaved (avi) format for manual segmentation.

To extract metadata corresponding to each file, we used the gdcmdump utility from the GDCM library. We were particularly interested in the time interval between adjacent frames, heart rate, number of columns and rows, and the dimensions in physical units (i.e. centimeters) corresponding to each pixel, as these would be needed for quantitative measurements of structure and function. We removed identifying information (name, birth date) and created a compressed metadata file corresponding to each study.

B. Convolutional Neural Network Based View Identification

We based our approach on the VGG architecture by Simonyan & Zisserman (K. Simonyan and A. Zisserman. Very deep convolutional networks for large-scale image recognition. arXiv 1409.1556 [cs.CV], 2014). The network takes in a fixed-sized input of grayscale images. e.g., with dimensions 224×224 pixels. Other pixel arrays can be used, which may be rectangular or square, or other shapes.

In one example embodiment, each image is passed through thirteen convolution layers, five max-pool layers, and three fully connected layers. Deeper networks, e.g., with 50-100 layers, may also be effective. The convolutional layers can include 3×3 filters, or dilated filters with a larger receptive field (e.g., up to 15 pixels×15 pixels), with stride 1 (the pixel spacing between filters), and max-pooling may be applied over a 2×2 window with stride 2. The stack of convolutions is followed by two fully connected layers, each with 500 hidden units, and a final fully connected layer with size output units. The output is fed into a six-way softmax layer to represent six different echo views: parasternal long-axis (PLAX), parasternal short-axis at the papillary muscle (PSAX), apical 2-, 3-, and 4-chamber (A2c, A3c, and A4c), and inferior vena cava (IVC). The view with the highest probability was selected as the predicted view. One example model, which focused on distinguishing occlusions as well as a broader set of views, had 22 classes.

Additionally, each echo contains periphery information unique to different output settings on ultrasound machines used to collect the data. This periphery information details additional details collected (i.e. electrocardiogram, blood pressure, etc.). To improve generalizability across institutions, we wanted the classification of views to use ultrasound data and not metadata presented in the periphery. Because periphery information is predominantly static between frames, we tracked pixels that do not change intensity over frames and created a mask to remove such pixels. Such pixels whose intensity does not change may correspond to a superimposed image or data, e.g., patient name that is burned into each image. Such a mask can avoid fitting to extraneous data, such as the ECG trace or details of the sampling rate. However, to account for small movement that does occur in the periphery information (i.e. ECG activity), we sampled multiple frames and removed pixels that were static for most frames.

Training data was comprised of 10 random frames from each manually labeled echo video. We trained our network on approximately 40,000 pre-processed images. For stochastic optimization, we used the ADAM optimizer with an initial learning rate of $1\times10^{-5}$ and mini-batch size of 64. For regularization, we applied a weight decay of $1\times10^{-4}$ and dropout with probability 0.5 on the fully connected layers. We ran our tests for 10-20 epochs or 10-20,000 iterations, which takes 1-2 hours on a Nvidia GTX 1080. Runtime per video was 600 ms on average.

C. Convolutional Neural Networks for Image Segmentation

Our CNN was based on the U-net architecture described by Ronneberger et al (O. Ronneberger, P. Fischer, and T. Brox. U-net: Convolutional networks for biomedical image segmentation. arXiv 1706.07342[cs.CV], 2015). In one implementation, the U-net network accepts a 512×512 pixel fixed-sized image as input, and is composed of a contracting path and an expanding path with a total of 23 convolutional layers. The contracting path is composed of ten convolutional layers with 3×3 filters followed by a rectified linear unit and four max pool layers, each using a 2×2 window with stride 2 for down-sampling. The expanding path is composed of eight convolutional layers with 3×3 filters followed by a rectified linear unit, and four 2×2 up-convolution layers. At every step in the expansion path (consisting of two convolutional layers), a concatenation with a cropped feature map from the corresponding step of the contracting path is performed to account for the loss of pixels at the border of every convolution of the contracting path. The final layer uses a 1×1 convolution to map each feature vector to the output classes, e.g., to determine the final probability of being in each class. Various numbers of layers in the different paths may be used, and different filter sizes can be used. We typically used between 16 and 19 convolutional layers.

Separate U-net CNN networks were trained to accept as input and perform segmentation on images from PLAX, PSAX (at the level of the papillary muscle), A4c and A2c views. Training data was derived for each class of echo view via manual segmentation. We performed data augmentation techniques on training data including cropping and blacking out random areas of the echo image. Such augmentation added noise so as to increase robustness of the model. As examples, training data can undergo varying degrees of cropping (or no cropping) at random x and y pixel coordinates. Similarly, circular areas of random size set at random locations in the echo image were set to 0-pixel intensity to achieve "blackout". This U-net architecture and data augmentation techniques enabled highly efficient training, achieving highly accurate segmentation from a relatively low number of training examples. Specifically, the PSAX segmentation U-net was trained using 72 manually segmented images, PLAX using 128 images, A4c using 168 images and A2c using 198 images. For all views, only 100-200 manually traced images were used for training. Every frame of every video may be segmented.

For stochastic optimization, we used the ADAM optimizer. Hyperparameters were optimized for each view-specific U-net, with initial learning rate set to $1\times10^{-4}$ or $1\times10^{-5}$, weight decay set to $1\times10^{-6}$, dropout set to 0.8 on the middle layers, and mini-batch size set to 5. The largest crop size and the largest blackout circle size were also tuned to each specific view with maximum crop size ranging from 40-75 pixels and maximum blackout size ranging from 30-50 pixels. We ran our tests for 150 epochs, which took approximately 2 hours for 200 training images on an Nvidia GTX 1080. In deploying the model, segmentation of each frame required 110 ms, on average.

D. Automated Measurements of Cardiac Structure and Function

We used the output of the CNN-based segmentation to compute chamber dimensions and ejection fraction. A typical echo reader typically filters through many videos to choose specific frames for measurement. They also rely on the electrocardiogram (ECG) tracing to phase the study and thus choose end-systole and end-diastole. Since our goal is to enable use of handheld echo devices without ECG capabilities, embodiments can use segmentation to indicate the portion of the cycle. Since there are likely to be chance errors in any CNN model, embodiment can average as many cardiac cycles as possible, both within one video and across videos.

1. LVEDVI, LVESVI, LVEF

Some embodiments can first use the time interval between frames and the patient heart rate to estimate the duration of the cardiac cycle, which is computed by taking the frames per second and dividing by cardiac cycles (i.e. heart beats) per second to get frames per cardiac cycle. A sliding window can be moved across the video with a window length of 90% of a cardiac cycle (thus avoiding seeing end-systole or end-diastole more than once). Using a window of less than a full cycle allows looking at each beat (peak contraction and peak relaxation) independently. Otherwise the 90th percentile may come from a different beat (relaxation sequence) than the 95th percentile. As examples, other window lengths can have any percentage less than 100%, e.g., 95%, 85%, 80%, etc. Within a window, we selected the 90% and 10% percentile of the left ventricular volumes to serve as LV end-diastolic area and end-systolic areas, respectively. Using 90% and 10% can be less noisy than using 100% and 0%. We derived left ventricular end diastolic volume (LVEDV) and left ventricular end systolic volume (LVESV) using the area-length formula. We also used these to compute an ejection fraction (EF) for that cycle.

To enable making multiple measurements per study, we moved a sliding window across the video with a step size of half of a cardiac cycle. A measurement was taken for each window position. At each measurement, a metric (e.g., volume, mass, length) of a structure was determined at a set of positions, e.g., at particular percentiles within the window, such as at 10%, 90%, and other percentiles of the maximum volume. In some embodiments, two percentile values can be selected for each metric: one percentile applied to measurements from multiple cycles within one video, and a second across all videos in a study. We selected the first percentile based on intuition regarding how the typical echo reader scans through images to select one for manual segmentation. We also avoided minimum and maximum values to exclude outliers from poor quality segmentation. We selected the second percentile to minimize bias between measured and automated values, although in most cases there was relatively little difference with choice of threshold and we used the median as default. As an example that can be used with multiple measurements from one video, we used 90% percentile for left ventricular end diastolic volume index (LVEDVI) and 50% percentile values (i.e. the median) for LVESI and left ventricular ejection fraction (LVEF). As an example that can be used across multiple videos in a study, we selected median values for LVEDVI, LVESI, and LVEF.

2. LAVOLI

For body-surface area indexed left atrial volume (LAVOLI), we took a similar approach, again taking the 90% percentile of the left atrium (LA) area for each window slid over the cardiac cycle. If there were multiple LAVOLI measurements from one video we took the median value, and if there were multiple videos per study, we took the median of these values. We found that erroneous LAVOLI values would arise from videos with an occluded LA. Although our view classification CNN was trained to discriminate these, some videos slipped through. We thus imposed an additional heuristic of excluding measurements from videos where LAVOLI/LVEDVI was less than 30%, as we found empirically that fewer than 5% of non-occluded studies had a ratio this extreme.

3. LVMI

For left ventricular mass (LVMI), we again took a sliding window approach, using the 90% percentile value for the LV outer (myocardial) area and computed LVMI using the Area-Length formula. If there were multiple LVMI measurements from one video we took the median value, and if there were multiple videos per study, we took the median of these values.

E. Automated Longitudinal Strain Measurements Using Speckle Tracking

Some embodiments use a strain computation adapted from an approach previously described by Rappaport and colleagues. Using the results of our image segmentation, we split the left ventricle along its long axis, and output images focused on the endocardial border of the hemi-ventricle. For a given frame, we used the trackpy Python package, a particle tracking software package, to locate speckles. A speckle is an echogenic (i.e. bright) structure in the image. The trackpy locate function allows the user to modify parameters involved in particle localization including particle diameter and minimum inter-particle separation.

To track a given speckle from frame to frame, we selected a multipixel patch surrounding it and then located the best match for that patch in the next frame using the matchTemplate function in the OpenCV package (with the TMCCOEFFNORMED statistic). Importantly, we limited the search space to that region that could be attained based on the maximum predicted velocity of the corresponding myocardial segment and excluded matches that fell below a threshold level of agreement (0.85). We then computed the displacement (in pixels) of the patch and projected the displacement onto the long axis of the ventricular segment. We fit a cubic polynomial function to estimate the variation in frame-to-frame longitudinal displacement with position along the long axis and computed its first derivative to obtain the strain rate, which is defined as the rate at which the distance of adjacent speckles changes with time.

We next used a rolling median (i.e., a median of values within a window centered at a point) to smooth the data and integrated the strain rate to obtain longitudinal strain. We selected the frame with the lowest (most negative) strain value across all segments to compute the global longitudinal strain, which incorporates the function of the septal portion of the left ventricle as well as the lateral wall. We also computed average longitudinal strain, deriving the minimum strain value across 25-30 positions along the length of the left or right ventricle, taken separately, and then computing a median across all positions.

We noted that images with very few successfully tracked speckles gave unstable estimates of longitudinal strain and thus we adaptively lowered the threshold level of agreement to include sufficient particles for function estimation for each frame. The median number of particles that passed the original filter was stored as a measure of quality for each video's strain estimate.

Estimation of strain can typically require 14 minutes per video, depending on the image size and the number of frames.

F. Disease Detection

1. Echocardiograms from Hypertrophic Cardiomyopathy and Cardiac Amyloidosis Patients We identified 225 patients who were seen at the UCSF Familial Cardiomyopathy Clinic for suspicion of hypertrophic cardiomyopathy. These patients typically had an affected family history or left ventricular hypertrophy with no clear alternative explanation. Patients had a variety of patterns of thickening including upper septal hypertrophy, concentric hypertrophy, and predominantly apical hypertrophy. We downloaded all echos within the UCSF database corresponding to these patients and confirmed evidence of hypertrophy. We excluded bicycle, treadmill, and dobutamine stress echo studies, as these tend to include slightly modified views or image annotations that could have confounding effects on models trained for disease detection.

Patients with cardiac amyloidosis were identified from probands seen at the UCSF Familial Cardiomyopathy Clinic and through a query of the UCSF echo database for reports including the term "amyloid". We identified 70 patients that had both 1) echocardiographic evidence of left ventricular hypertrophy and/or echocardiographic suspicion of cardiac amyloidosis and 2) confirmation of amyloid disease by tissue biopsy, nuclear medicine scan, cardiac MRI, or genetic testing (transthyretin variant). We downloaded all echos within the UCSF database corresponding to these patients.

Controls patients were also selected from the UCSF echo database. For each HCM and amyloid case, up to 5 matched controls were selected, with matching by age, sex, year of study, ultrasound device manufacturer and model.

2. CNNs to Detect HCM and Cardiac Amyloidosis

In addition to extracting measurements from segmentations, we also set out to develop a classifier to automate disease identification. The two diseases we targeted here are HCM and cardiac amyloidosis. Again, we based our approach on the VGG architecture by Simonyan & Zisserman with a similar network architecture as the one used in view classification, but with 16 layers instead of 13. The stack of convolutions is followed by two fully connected layers, each with 4096 hidden units, and a final fully connected layer with 2 output units. This final layer is fed into a 2-class softmax layer to represent probabilities for HCM vs. control or amyloid vs. control.

To maintain consistency between inputs fed into the neural network, we extracted pairs of images from each video that corresponded to end-diastole and end-systole and fed these into our neural network. Images were resized to 224×224 and consequently, our input pair had dimensions 224×224×2. Other pixel sizes may be used. To locate the end-diastole and end-systole frames in a video, we used the segmentation networks for PLAX and A4c views to extract left ventricular area values from each frame in the video. We applied a rolling median over the area values and took the frame with the 90th percentile area as the end diastole frame and the 10th percentile frame as the end systole frame. Other criteria may be used, e.g., different percentages or using a rolling average as opposed to median, and different percentiles can be selected for end-systole and end-diastole.

We trained separate networks for HCM and amyloid. For stochastic optimization, we used the ADAM optimizer with an initial learning rate of $1 \times 10^{-5}$ and mini-batch size of 64. For regularization, we applied a weight decay of $1 \times 10^{-5}$ and dropout with probability 0.5 on the fully connected layers. We ran our tests for 50 epochs, which took one hour to run on an Nvidia GTX 1080. Run-time performance was approximately 600 ms per video.

Accuracy was assessed using internal 5-fold cross-validation. Given that a given patient typically had multiple studies, training and test sets were defined by patient (i.e. medical record number) rather than by study. We performed four rounds of cross-validation for each view (PLAX and A4c). The score for each study i was obtained by: 1) taking a median probability $p_{ij}$ across the 4-rounds of cross-validation for each video j; 2) taking a median of these $p_{ij}$ values for all videos in a study corresponding to a given view, resulting in $p_{PLAX_i}$ and $p_{A4c_i}$; 3) averaging the A4c and PLAX values to obtain $p_i$.

As an independent measure of interpretability of our disease detection models, we derived the Spearman correlation coefficient of $p_i$ values with left ventricular mass index and left atrial volume index values for the corresponding study, analyzing cases and controls separately.

G. Statistical Analysis

All analysis was performed using R 3.3.2. The linear regression of absolute deviation between manual and automated values of LVEDVI was computed using the standard lm function in R. We applied a square root transform to the absolute deviation, which made the residuals approximately normal in distribution (untransformed and log-transformed values were right- and left-skewed, respectively). To assess the chance difference between values of Spearman correlation coefficients for 7 metrics of internal consistency (LAVOLI vs. LVEF, LAVOLI vs. LVMI, LAVOLI vs. LVEDVI, LAVOLI vs. LVESVI, GLS vs LVEF, GLS vs LVEDVI, GLS vs LVESVI), we resampled with replacement (i.e. bootstrap) the input data for each comparison 10.000 times, recomputed the correlation coefficient for automated and manual values, and took the mean of the difference across all 7 metrics. The p-value was taken as the relative frequency of observing a difference of 0 or less (i.e. manual measurements are superior) in the 10,000 iterations.

V. Method

Figure 10:
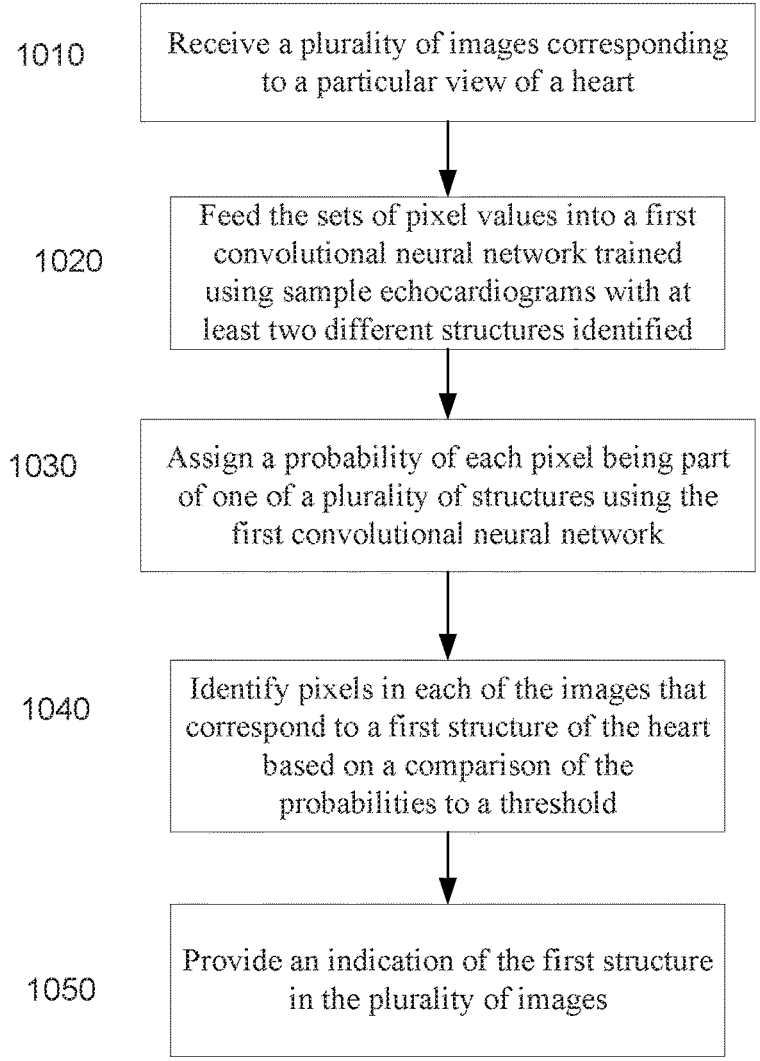
FIG. 10 is a flowchart illustrating a method of performing an analysis on echocardiograms.

FIG. 10 is a flowchart illustrating a method 1000 of performing an analysis on echocardiograms. Method 1000 can analyze images obtained from an echocardiogram. Method 1000 may be performed by a computer system, as described herein.

At block 1010, a plurality of images corresponding to a particular view of a heart are received. Each of the images includes a set of pixel values. The plurality of images corresponding to the particular view of the heart can be identified using a convolutional neural network, e.g., as described herein, such as in sections II.A and IV.B. A probability can be provided for each image (or entire echo) as to which view it is from, and certain images (or whole echos) can be discarded if a probability is below a threshold. The images can be preprocessed as described in section IV.A. The images can be received via various communications channels (e.g., wireless or wired) and stored in memory. The set of pixels of an image can be stored with an indication of a start and end of the set of pixels corresponding to a particular image.

At block 1020, the sets of pixel values are fed into a first convolutional neural network trained using sample echocardiograms with at least two different structures identified. The first convolutional neural network can performed segmentation, e.g., as described in sections II.B and IV.C. The sets of pixel values can be read from memory into a processor (e.g., into working memory or cache), and then provided to a first layer of the neural network, which can apply weights, kernels, and/or activation functions (e.g., sigmoidal or softmax functions) to obtain intermediate results that are fed into further layers. Not all of the echocardiograms need to have two structures identified but at least some of them would have more than two, e.g., different chambers of the heart.

At block 1030, for each pixel of each image, a probability of the pixel being part of one of a plurality of structures is assigned using the first convolutional neural network. At least one of the structures can be part of a heart imaged in the echocardiogram. The structures can be as described herein, e.g., left/right atria and left/right ventricles. In some implementations, a structure of "other" can be used, as well as other structures, as may be described herein. In various embodiments, a probability may be determined for a pixel to be assigned to each of the plurality of structures. A maximum probability may be determined. One or all of the probability can be provided to later stages of the pipeline.

At block 1040, a set of pixels in each of the images that correspond to a first structure of the heart is identified based on a comparison of the probabilities to a threshold. It is possible that a pixel is not assigned to any structure, e.g., of none of the probabilities are sufficiently high. It is also possible that a pixel is assigned to two structures, although some implementations can restrict a pixel to only be assigned to one structure.

At block 1050, an indication of the first structure in the plurality of images is provided. For example, the first structure can be displayed in a highlighted manner. Thus, the indication of the first structure can be provided to a display. As another example, certain pixels of a structure can be provided to another routine, e.g., to computer properties or function of the structure. For instance, the indication of the first structure in the plurality of images can be provided to a structure module, which determines a structural property of the first structure based on the identified pixels corresponding to the first structure. For instance, a length can be associated with each pixel, e.g., based on a height and possibly weight of the subject. The pixels assigned to a structure based on the segmentation can then be counted to determine a length. As other examples, the structural property can be volume or mass. Such counting of pixels can also be used to determine the volume and mass. Such structural properties are described in more detail above.

In other embodiments, the indication of the first structure in the plurality of images is provided to a function module, which determines a functional property of the first structure based on the identified pixels corresponding to the first structure. As examples, the functional property is ejection fraction or strain. Such functional properties are described in more detail above.

In some embodiments, the images can be phased, e.g., as described herein. The phasing of images can be performed such that the first structure is identified to determine a set of images corresponding to a particular part of a cardiac cycle. The structures can be identified view segmentation, e.g., as described herein. The identified pixels of the first structure can be fed in the set of images to a second convolutional neural network that is trained based on samples that have a disease and do not have a disease. Other sets of images corresponding to a different part of the cardiac cycle for the first structure can be fed into the second convolutional neural network.

After a disease is detected, the subject can be treated. As examples, such treatments can include behavioral changes (e.g., avoidance of high intensity exercise), medication, and implantation of a cardiac defibrillator.

VI. Computer System

Any of the computer systems mentioned herein may utilize any suitable number of subsystems. Examples of such subsystems are shown in FIG. 11 in computer system 10. In some embodiments, a computer system includes a single computer apparatus, where the subsystems can be the components of the computer apparatus. In other embodiments, a computer system can include multiple computer apparatuses, each being a subsystem, with internal components. A computer system can include desktop and laptop computers, tablets, mobile phones and other mobile devices.

The subsystems shown in FIG. 11 are interconnected via a system bus 75. Additional subsystems such as a printer 74, keyboard 78, storage device(s) 79, monitor 76, which is coupled to display adapter 82, and others are shown. Peripherals and input/output (I/O) devices, which couple to I/O controller 71, can be connected to the computer system by any number of means known in the art such as input/output (I/O) port 77 (e.g., USB, FireWire®). For example, I/O port 77 or external interface 81 (e.g. Ethernet, Wi-Fi, etc.) can be used to connect computer system 10 to a wide area network such as the Internet, a mouse input device, or a scanner. The interconnection via system bus 75 allows the central processor 73 to communicate with each subsystem and to control the execution of a plurality of instructions from system memory 72 or the storage device(s) 79 (e.g., a fixed disk, such as a hard drive, or optical disk), as well as the exchange of information between subsystems. The system memory 72 and/or the storage device(s) 79 may embody a computer readable medium. Another subsystem is a data collection device 85, such as a camera, microphone, accelerometer, and the like. Any of the data mentioned herein can be output from one component to another component and can be output to the user.

A computer system can include a plurality of the same components or subsystems, e.g., connected together by external interface 81, by an internal interface, or via removable storage devices that can be connected and removed from one component to another component. In some embodiments, computer systems, subsystem, or apparatuses can communicate over a network. In such instances, one computer can be considered a client and another computer a server, where each can be part of a same computer system. A client and a server can each include multiple systems, subsystems, or components.

Aspects of embodiments can be implemented in the form of control logic using hardware circuitry (e.g. an application specific integrated circuit or field programmable gate array) and/or using computer software with a generally programmable processor in a modular or integrated manner. As used herein, a processor can include a single-core processor, multi-core processor on a same integrated chip, or multiple processing units on a single circuit board or networked, as well as dedicated hardware. Based on the disclosure and teachings provided herein, a person of ordinary skill in the art will know and appreciate other ways and/or methods to implement embodiments of the present invention using hardware and a combination of hardware and software.

Any of the software components or functions described in this application may be implemented as software code to be executed by a processor using any suitable computer language such as, for example, Java, C, C++, C#, Objective-C, Swift, or scripting language such as Perl or Python using, for example, conventional or object-oriented techniques. The software code may be stored as a series of instructions or commands on a computer readable medium for storage and/or transmission. A suitable non-transitory computer readable medium can include random access memory (RAM), a read only memory (ROM), a magnetic medium such as a hard-drive or a floppy disk, or an optical medium such as a compact disk (CD) or DVD (digital versatile disk), flash memory, and the like. The computer readable medium may be any combination of such storage or transmission devices.

Such programs may also be encoded and transmitted using carrier signals adapted for transmission via wired, optical, and/or wireless networks conforming to a variety of protocols, including the Internet. As such, a computer readable medium may be created using a data signal encoded with such programs. Computer readable media encoded with the program code may be packaged with a compatible device or provided separately from other devices (e.g., via Internet download). Any such computer readable medium may reside on or within a single computer product (e.g. a hard drive, a CD, or an entire computer system), and may be present on or within different computer products within a system or network. A computer system may include a monitor, printer, or other suitable display for providing any of the results mentioned herein to a user.

Any of the methods described herein may be totally or partially performed with a computer system including one or more processors, which can be configured to perform the steps. Thus, embodiments can be directed to computer systems configured to perform the steps of any of the methods described herein, potentially with different components performing a respective step or a respective group of steps. Although presented as numbered steps, steps of methods herein can be performed at a same time or at different times or in a different order. Additionally, portions of these steps may be used with portions of other steps from other methods. Also, all or portions of a step may be optional. Additionally, any of the steps of any of the methods can be performed with modules, units, circuits, or other means of a system for performing these steps.

The specific details of particular embodiments may be combined in any suitable manner without departing from the spirit and scope of embodiments of the invention. However, other embodiments of the invention may be directed to specific embodiments relating to each individual aspect, or specific combinations of these individual aspects.

The above description of example embodiments of the invention has been presented for the purposes of illustration and description. It is not intended to be exhaustive or to limit the invention to the precise form described, and many modifications and variations are possible in light of the teaching above.

A recitation of "a", "an" or "the" is intended to mean "one or more" unless specifically indicated to the contrary. The use of "or" is intended to mean an "inclusive or," and not an "exclusive or" unless specifically indicated to the contrary. Reference to a "first" component does not necessarily require that a second component be provided. Moreover reference to a "first" or a "second" component does not limit the referenced component to a particular location unless expressly stated. The term "based on" is intended to mean "based at least in part on."

All patents, patent applications, publications, and descriptions mentioned herein are incorporated by reference in their entirety for all purposes. None is admitted to be prior art.

What is claimed is:

1. A method of analyzing images obtained from an echocardiogram, the method comprising performing by a computer system:
    receiving the images obtained from the echocardiogram;
    identifying a subset of images corresponding to a particular echo view of a heart using a first convolutional neural network, wherein each image of the subset of images includes a set of pixel values, and wherein the particular echo view is selected from a group consisting of apical 2-, 3-, and 4-chamber (A2c, A3c, and A4c), parasternal long axis (PLAX), parasternal short axis (PSAX), and inferior vena cava (IVC);
    feeding the sets of pixel values into a second convolutional neural network trained using sample echocardiograms with at least two different structures identified;
    for each pixel of each image of the subset of images, assigning a probability of the pixel being part of one of a plurality of structures using the second convolutional neural network, wherein at least one of the plurality of structures is part of the heart imaged in the echocardiogram;
    identifying pixels in each of the images that correspond to a first structure of the heart based on a comparison of the probabilities to a threshold; and
    providing an indication of the first structure in the subset of images.

2. The method of claim 1, wherein the indication of the first structure is provided to a display.

3. The method of claim 1, further comprising:
 determining a structural property of the first structure based on the identified pixels corresponding to the first structure in each of the subset of images.

4. The method of claim 3, wherein the structural property is volume or mass.

5. The method of claim 1, further comprising:
 determining a functional property of the first structure based on the identified pixels corresponding to the first structure in each of the subset of images.

6. The method of claim 5, wherein the functional property is an ejection fraction or a strain.

7. The method of claim 1, further comprising:
 phasing images in which the first structure is identified to determine a set of images corresponding to a particular stage of a cardiac cycle; and
 feeding the identified pixels of the first structure in the set of images to a third convolutional neural network that is trained based on samples that have a disease and do not have the disease.

8. The method of claim 7, further comprising:
 feeding other sets of images corresponding to a different part of the cardiac cycle for the first structure into the second convolutional neural network.

9. The method of claim 1, further comprising:
 identifying another subset of images corresponding to a different echo view of the heart using a fourth convolutional neural network, wherein each image of the other subset of images includes another set of pixel values, and wherein the different echo view is different from the particular echo view;
 feeding the other sets of pixel values into a fifth convolutional neural network trained using sample echocardiograms with at least two different structures identified;
 for each pixel of each image of the other subset of images, assigning another probability of the pixel being part of one of the plurality of structures using the fifth convolutional neural network;
 identifying pixels in each of the images that correspond to the first structure of the heart based on a comparison of the other probabilities to the threshold; and
 providing another indication of the first structure in the other subset of images.

10. A computer product comprising a non-transitory computer readable medium storing a plurality of instructions that when executed control a computer system to perform operations for analyzing images obtained from an echocardiogram, the operations comprising:
 receiving the images obtained from the echocardiogram;
 identifying a subset of images corresponding to a particular echo view of a heart using a first convolutional neural network, wherein each image of the subset of images includes a set of pixel values, and wherein the particular echo view is selected from a group consisting of apical 2-, 3-, and 4-chamber (A2c, A3c, and A4c), parasternal long axis (PLAX), parasternal short axis (PSAX), and inferior vena cava (IVC);
 feeding the sets of pixel values into a second convolutional neural network trained using sample echocardiograms with at least two different structures identified;
 for each pixel of each image of the subset of images, assigning a probability of the pixel being part of one of a plurality of structures using the second convolutional neural network, wherein at least one of the plurality of structures is part of the heart imaged in the echocardiogram;
 identifying pixels in each of the images that correspond to a first structure of the heart based on a comparison of the probabilities to a threshold; and
 providing an indication of the first structure in the subset of images.

11. The computer product of claim 10, wherein the indication of the first structure is provided to a display.

12. The computer product of claim 10, wherein the operations further comprise:
 determining a structural property of the first structure based on the identified pixels corresponding to the first structure in each of the subset of images.

13. The computer product of claim 12, wherein the structural property is volume or mass.

14. The computer product of claim 10, wherein the operations further comprise:
 determining a functional property of the first structure based on the identified pixels corresponding to the first structure in each of the subset of images.

15. The computer product of claim 14, wherein the functional property is an ejection fraction or a strain.

16. The computer product of claim 10, wherein the operations further comprise:
 phasing images in which the first structure is identified to determine a set of images corresponding to a particular stage of a cardiac cycle; and
 feeding the identified pixels of the first structure in the set of images to a third convolutional neural network that is trained based on samples that have a disease and do not have the disease.

17. The computer product of claim 16, wherein the operations further comprise:
 feeding other sets of images corresponding to a different part of the cardiac cycle for the first structure into the second convolutional neural network.

18. The computer product of claim 10, wherein the operations further comprise:
 identifying another subset of images corresponding to a different echo view of the heart using a fourth convolutional neural network, wherein each image of the other subset of images includes another set of pixel values, and wherein the different echo view is different from the particular echo view;
 feeding the other sets of pixel values into a fifth convolutional neural network trained using sample echocardiograms with at least two different structures identified;
 for each pixel of each image of the other subset of images, assigning another probability of the pixel being part of one of the plurality of structures using the fifth convolutional neural network;
 identifying pixels in each of the images that correspond to the first structure of the heart based on a comparison of the other probabilities to the threshold; and
 providing another indication of the first structure in the other subset of images.

* * * * *